US006087168A

United States Patent [19]
Levesque et al.

[11] Patent Number: 6,087,168
[45] Date of Patent: Jul. 11, 2000

[54] CONVERSION OF NON-NEURONAL CELLS INTO NEURONS: TRANSDIFFERENTIATION OF EPIDERMAL CELLS

[75] Inventors: Michel F. Levesque, Beverly Hills; Toomas Neuman, Santa Monica, both of Calif.

[73] Assignee: Cedars Sinai Medical Center, Los Angeles, Calif.

[21] Appl. No.: 09/234,332

[22] Filed: Jan. 20, 1999

[51] Int. Cl.[7] ............................ C12N 15/10; C12N 15/09; C12N 15/11

[52] U.S. Cl. ........................ 435/345; 435/325; 435/366; 435/455

[58] Field of Search .............................. 435/6, 7.21, 91.1, 435/325, 366, 375, 377, 384; 536/23.1, 24.3, 24.5

[56] References Cited

U.S. PATENT DOCUMENTS

| | | | |
|---|---|---|---|
| 5,411,883 | 5/1995 | Boss et al. | 435/240.2 |
| 5,589,376 | 12/1996 | Anderson et al. | 435/240.2 |
| 5,753,506 | 5/1998 | Johe | 435/377 |

OTHER PUBLICATIONS

Branch TIBS 23 pp. 45–50, Feb. 1998.
Flanagan et al., Nature Biotech. 17:48–52, Jan. 1999
Jensen, Peter K.A. et al., Low $Ca^{2+}$ Stripping of DIfferentiating Cell Layers in Human Epidermal Cultures: An in Vitro Model of Epidermal Regeneration, *Experimental Cell Research,* vol. 175, pp. 63–73 (1988).
Kalyani, Anjali J. et al., Spinal Cord Neuronal Precursors Generate Multiple Neuronal Phenotypes in Culture, *The Journal of Neuroscience,* vol. 18, No. 19, pp. 7856–7868 (Oct. 1, 1998).
Stemple, Derek L., Neural Stem Cells Are Blasting Off, *Neuron,* vol. 18, No. 1–4, pp. 1–4 (Jan. 1997).
Renoncourt, Yannick, Neurons derived in vitro from ES cells express homeoproteins characteristic of motoneurons and interneurons, *Mechanisms of Development,* vol. 79, pp. 185–197 (1998).
Bellefroid, Eric J. et al., "X–MyT1, a Xenopus C2HC–Type Zinc Finger Protein with a Regulatory Function in Neuronal Differentiation," Cell, vol. 87, pp. 1191–1202, Dec. 27, 1996.
Ishibashi, Makoto et al., "Targeted disruption of mammalian hairy and Enchancer of split homolog–1 (hes–1) leads to up–regulation of neural helix—loop—helix factors, premature neurogenesis, and severe neural tube defects," Genes & Development, vol. 9, pp. 3136–3148, 1995.
Ishibashi, Makoto et al., "Persistent expression of helix—loop–helix factor HES–1 prevens mammalian neural differentiation in the central nervous system," The EMBO Journal, vol. 13, No. 8, pp. 1799–1805, 1994.
Lee, Jacqueline E. et al., "Conversion of Xenopus Ectoderm into Neurons by NeuroD, a Basic Helix–Loop–Helix Protein," Science, vol. 268, pp. 836–844, May 12, 1995.
Ma, Qiufu et al., "Identification of neurogenin, a Vertebrate Neuronal Determination Gene," Cell, vol. 87, pp. 43–52, Oct. 4, 1996.
McCormick, Mary B., et al., "neuroD2 and NeuroD3: Distinct Expression Patterns and Transcriptional Activation Potentials within the neuroD Gene Family," Molecular and Cellular Biology, vol. 16, No. 10, pp. 5792–5800, Oct., 1996.
Wickelgren, I., "Teaching the Spinal Cord to Walk," Research News, Science, vol. 279, pp. 319–321, Jan. 16, 1998.
Nakata, Katsunori et al., "Xenopus Zic3, a primary regulator both in neural and neural crest development," Proc. Natl. Acad. Sci. USA, Developmental Biology, vol. 94, pp. 11980–11985, Oct. 1997.
Tanabe, Yasuto et al., Diversity and Pattern in the Developing Spinal Cord, Science, vol. 274, pp. 1115–1123, Nov. 15, 1996.
Suzuki, Atsushi et al., "Xenopus msx1 mediates epidermal induction and neural inhibition by BMP4," Development, vol. 124, pp. 3037–3044, 1997.

*Primary Examiner*—George C. Elliott
*Assistant Examiner*—Melissa Schmidt
*Attorney, Agent, or Firm*—Pretty, Schroeder & Poplawski, P.C.

[57] ABSTRACT

The present invention is directed to method of converting, or transdifferentiating the epidermal cells into viable neurons useful in both cell therapy and gene therapy treatment methodologies. The method of transdifferentiating epidermal cells into neuronal cells comprises the following steps: obtaining skin cells from a patient; dedifferentiating these cells with an appropriate medium, neurotrophin or cytokine; transfecting the skin cells with one or more expression vector(s) encoding at least one neurogenic transcription factor or active fragments thereof; expressing at least one of the neurogenic transcription factors; growing the transfected cells in an appropriate medium; and adding to the medium one or more antisense oligonucleotide(s) corresponding to at least one negative regulator of neuronal differentiation, whereby the epidermal cells are transdifferentiated into neuronal cells.

15 Claims, 2 Drawing Sheets

CONVERSION OF NON-NEURONAL CELLS INTO NEURONS: TRANSDIFFERENTIATION OF EPIDERMAL CELLS

BACKGROUND OF THE INVENTION

The human nervous system comprises highly diverse neuronal cell types that make specific interconnections with one another. Once destroyed, neuronal cells are not regenerative. Thus, there is a long felt need in the biomedical field to be able to generate neurons for use in the treatment of various neurological disorders via either the direct transfer of neuronal cells in a cell therapy approach, or by delivery of potential genetically based drugs, such as nerve growth factors, in a gene therapy approach.

For example, in the case of neurotrauma, stroke and neurodegenerative diseases, such as Parkinson disease, Huntington disease, and Alzheimer disease, the most comprehensive approach to regain neural function is via direct cell therapy to replace the damaged cells with healthy cells. In this cell therapy application, newly generated neurons would be utilized by direct transfer, via grafting and/or transplantation, to a patient in need.

A gene therapy approach, on the other hand, is needed to treat other types of nervous system disorders. Because the brain is protected by a blood-brain barrier that effectively blocks the flow of large molecules into the brain, peripheral injection of potential growth factor drugs, or other potentially therapeutic gene products, is ineffective. Thus, a major challenge facing the biotechnology industry is to find an efficient mechanism for delivering potential gene therapy products, directly to the brain, so as to treat neurological disorders on the molecular level. In this regard, a renewable source of human neural cells could serve as a vehicle to deliver potential gene therapy products to the brain and nervous system.

A major problem, however, for the further progression of neuronal transplantation for the purpose of either cell therapy or gene therapy is the source of donor material. To date, numerous therapeutic transplantations have been performed exploiting various types of human fetal tissue as the source of donor material. Significant ethical and technical issues arise, however, with the use of human fetal tissue as donor material. Examples of technical problems associated with the use of fetal tissue are immunological rejection of the donor material by the host and risk of transmitting disease to the host by the transplanted neuronal cells.

Thus, there is a need in the field of neurological research and applied neurobiology for a renewable source of neurons for use in both cell therapy and gene therapy. Importantly, the use of such cells could eliminate a need for fetal human tissue in therapeutic approaches aimed at restoring neurological function by intracerebral transplantation of nervous system cells.

SUMMARY OF THE INVENTION

The present invention is directed to methods of converting, or transdifferentiating, epidermal cells into different types of neuronal cells having numerous uses in the field of applied neurobiology. In particular, the newly created neurons of the invention can be used in both cell therapies and gene therapies aimed at alleviating neurological disorders and diseases. Further, the invention obviates the need for human fetal tissue as a renewable source of neurons to be used in various medical and research applications.

In accordance with the present invention, the method of converting epidermal basal cells into newly created neurons begins with obtaining epidermal cells from a patient's skin. The isolated cells are then dedifferentiated using a calcium free media. This step is followed by transfecting the epidermal cells with one or more expression vector(s) containing at least one cDNA encoding a neurogenic transcription factor responsible for neural differentiation. Suitable cDNAs include that basic-helix-loop-helix activators, such as NeuroD1, NeuroD2, ASH1, and zinc-finger type activators, such as Zic3, and MyT1. The transcription factors are preferably of human origin, but homologous, non-human counterparts can also be utilized in the invention. The transfection step is followed by expressing, or overexpressing, at least one of the neurogenic transcription factors, while simultaneously, or near simultaneously, deactivating factors that are responsible for suppressing neuronal differentiation. This latter step is accomplished by adding at least one antisense oligonucleotide known to suppress neuronal differentiation to the growth medium, such as the human MSX1 gene and/or the human HES1 gene (or non-human, homologous counterparts). Preferably, the antisense oligonucleotide is thio-modified. Finally, the transfected cells are grown in the presence of a retinoid and a least one neurotrophin or cytokine, such as brain derived neurotrophic factor (BDNF), nerve growth factor (NGF), neurotrophin 3 (NT-3), neurotrophin 4 (NT-4). This novel process leads to the conversion of the epidermal cells into transdifferentiated neuronal cells.

Another aspect of the present invention is the newly created neuronal cell itself. Such a cell is of non-neuronal origin, preferably from an epidermal cell. The transdifferentiation process of the invention converts this non-neuronal cell into a cell that exhibits a morphological, physiological and/or immunological feature of viable neurons. Moreover, some of the transdifferentiation neurons display a morphological, physiological and/or immunological feature of an astroglial cell, such as expression of glial fibrillary acidic protein.

Significantly, the cell product of the novel transdifferentiation protocol of the present invention can be utilized in both cell and gene therapies aimed at alleviating various neurological diseases and disorders. The cell therapy approach involves the use of autologous transplantation of the newly created neuronal cells as a treatment for brain or spinal cord injury, stroke and neurodegenerative diseases. The steps in this application include: first transdifferentiating epidermal cells, as described herein, then allowing the newly created neuronal cells to form functional connections either before of after a step involving transplantation of the transdifferentiated neurons. The gene therapy approach, on the other hand, also involves transdifferentiating epidermal cells, however, following the transdifferentiation step, the newly created neurons are then transfected with an appropriate vector containing a cDNA for a desired secretable regulatory factor, followed by a step where the modified transdifferentiated neurons are transplanted.

In either a cell or gene therapy approach, therefore, the transdifferentiated neurons of the present invention can be autologously transplanted in, or grafted to, a patient in need. Thus, the neuronal cells of the invention can be used to replace neurons in a patient in a cell therapy approach, useful in the treatment of brain or spinal cord injury, stroke and neurodegenerative diseases. Or, these neuronal cells can be used as vehicles for the delivery of specific gene products to the neurological system. One example of how these newly created neurons can be used in a gene therapy methodology is in alleviating the effects of Parkinson's disease. Specifically, the delivery of tyrosine hydrolase, a key enzyme in dopamine synthesis, via the transplantation of neuronal cells of the present invention, which have been transfected with a vector suitable for the expression of tyrosine hydrolase, is one example of the use of these newly created neurons in gene therapy.

Still another aspect of the invention is a kit for converting epidermal cells to neuronal cells, which includes the appropriate expression vectors and reagents for the novel transdifferentiation process of the present invention. This kit preferably would include the following expression vectors and reagents: one or more expression vector(s) containing cDNA(s) encoding a neurogenic transcription factor, or fragment(s) thereof, such as NeuroD1, NeuroD2, ASH1, Zic3, and MyT1, or non-human, homologous counterparts, at least one antisense oligonucleotide corresponding to a portion of the human MSX1 gene and/or the human HES1 gene, or non-human, homologous counterparts, a retinoid and at least one neurotrophin, such as BDNF, NGF, NT-3, NT-4, and instructions for use with a patient's own skin cells.

DETAILED DESCRIPTION OF THE PREFERRED EMBODIMENTS OF THE INVENTION

Figure 1A:
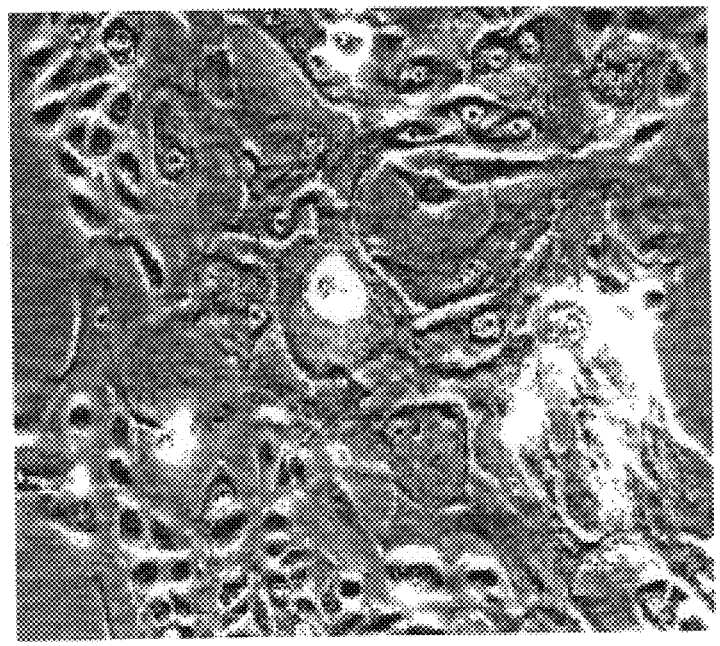
FIG. 1A, 1B and 1C. Transdifferentiation of epidermal basal cells into neuronal cells. Dedifferentiated epidermal basal cells were transfected with NeuroD1+Zic1+MyT1 and simultaneously treated with antisense oligonucleotides corresponding to a portion of MSX1 and HES transcription factors. (A) epidermal basal cells, (B) dedifferentiated epidermal basal cells, (C) newly created neurons, 25% of cells are Neurofilament M immunoreactive 5 days after transfection and treatment with BDNF and all-trans retinoic acid.
Figure 1B:
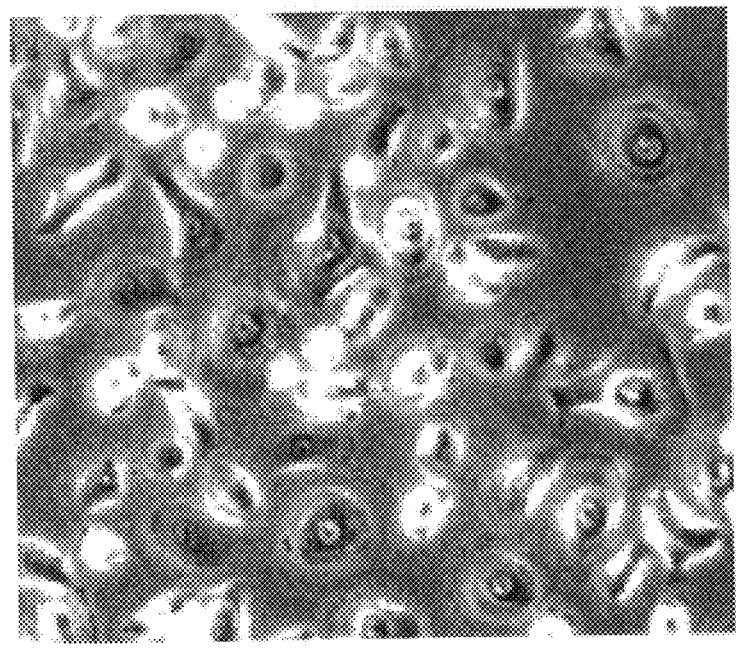
Figure 1C:
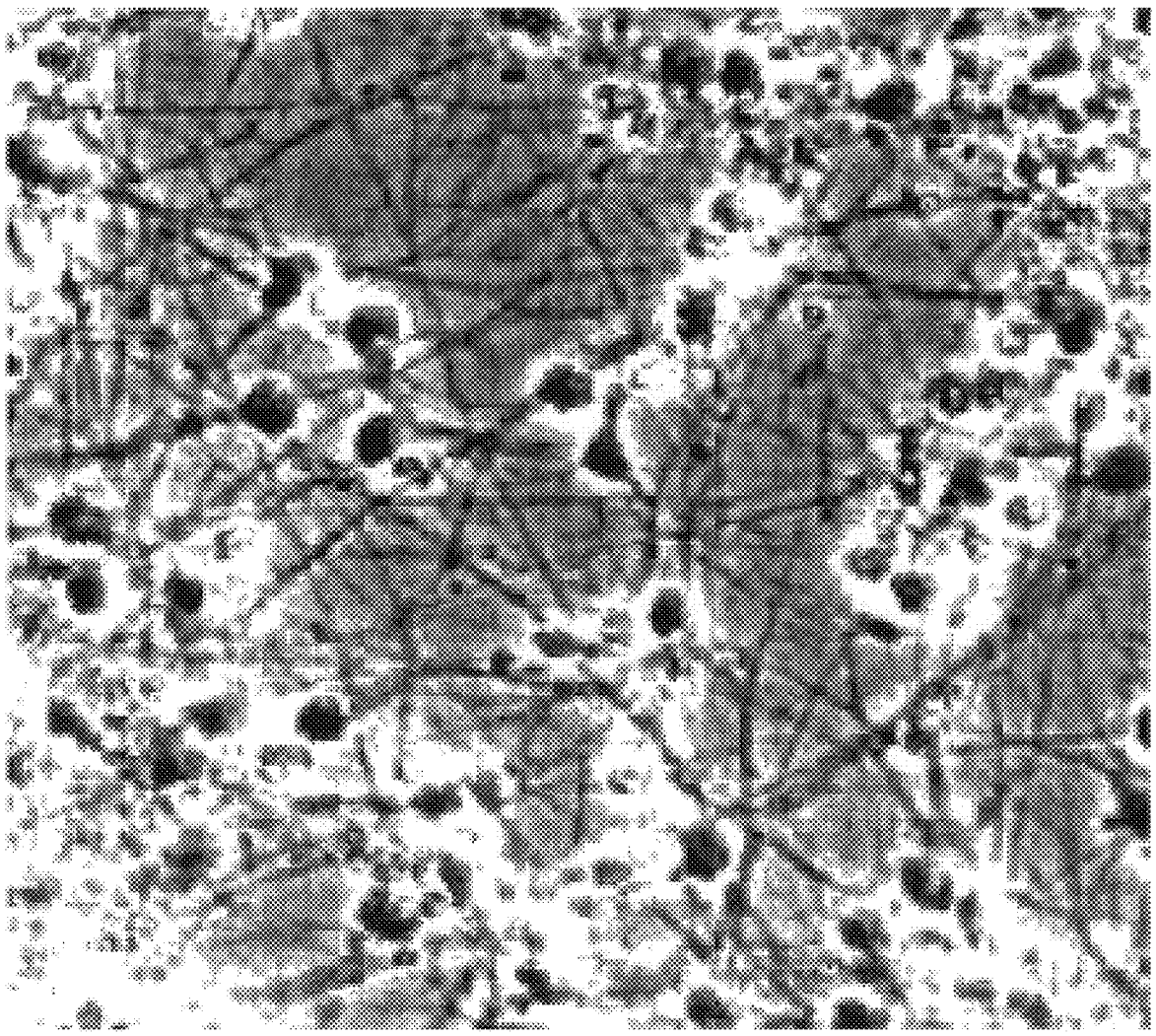

An awareness of the difficulties currently associated with neuronal cell or gene therapy approaches, as these pertain to the use of alternative sources of neuronal cells, especially those used for autologous transplantation, has led to the present invention. The present invention provides methods to convert, or transdifferentiate, epidermal cells into different types of neuronal cells that can be used for intracerebral transplantation. Importantly, the present invention also allows for genetic manipulation of the newly created neurons.

A significant aspect of the present invention is that it permits the use of a patient's own cells to develop different types of neuronal cells that can be transplanted after in vitro growth and transdifferentiation. Thus, this technology eliminates the problems associated with transplantation of non-host cells, such as, immunological rejection and the risk of transmitting disease.

The present invention can be used to generate neurons from an individual patient, thus making autologous transplantations possible as a treatment modality for many neurological conditions including neurotrauma, stroke, neurodegenerative diseases such as Parkinson's disease, Huntington disease, Alzheimer's diseases. Thus, the invention provides for neurological therapies to treat the disease or trauma of interest.

To summarize, this technology provides a plentiful source of neurons for clinical treatments which require transplantation of neurons 1) to compensate for a loss of host neurons or 2) as vehicles to deliver genetically-based drugs. Further, the invention provides a novel neurological tool for use in basic research and drug screening.

I. Theoretical Molecular Basis of the Invention

Neuronal development requires orchestrated action of numerous molecular processes including epigenetic signaling and activation of specific transcription factor systems. During development, ectodermal cells develop into neuronal tissue or epidermis, depending on the signals they receive from the surrounding cells. At this early developmental stage, activation of various members of the bone morphogenetic protein family (BMP) of growth factors results in epidermal differentiation, while blocking their action results in neuronal differentiation. (See Tanabe and Jessel, 1996, for a review.) This differentiation pathway is due to the action of BMP growth factors which induce expression of the homeodomain transcription factor MSX1 in ectodermal cells. Once MSX1 is expressed, induction of the neuronal determination genes is simultaneously suppressed and neuronal differentiation inhibited. (Suzuki et al., 1997).

Alternatively, retinoic acid and Sonic Hedgehog (SHH) signaling are responsible for the induction of expression of several neuronal determination and differentiation genes whose activity is essential for neuronal differentiation. (See Tanabe and Jessel, 1996, for a review.) In particular, data demonstrate that over-expression of several neurogenic basic Helix-Loop-Helix (bHLH) and Zinc-finger transcription factors results in conversion of non-determined ectoderm into neuronal tissue. Additionally, forced expression of bHLH transcription factors, NeuroD1, NeuroD2 (Lee et al., 1995, McCormick et al., 1996), or neurogenin 1 (Ma et al., 1996, McCormick et al., 1996), or Zinc-finger transcription factors MyT1 (Bellefroid et al., 1996) or Zic3 (Nakata et al., 1997) results in induction of additional neurogenic transcription factors and initiation of neuronal differentiation of amphibian ectodermal cells.

Moreover, at the level of gene regulation, the effect of neurogenic bHLH transcription factors is antagonized by the HES family of transcription factors which are known to suppress transcription. Over-expression of HES1 protein in developing neuronal cells blocks neuronal differentiation (Ishibashi et al., 1994), whereas blocking its expression stimulates neuronal differentiation (Ishibashi et al., 1995). Thus, neuronal differentiation, like other biological process, is regulated by both positive and negative factors.

The molecular regulatory mechanisms known to be operational during amphibian development were used as the theoretical basis for the present invention. The methods and cell products of the invention are based on the discovery that induced expression of a transcription factor that positively regulates human neuronal differentiation, performed in concert with the suppression of a negative regulator of human neuronal differentiation, results in the conversion of epidermal cells into newly created neurons.

In particular, the inventive methods of the present invention provide for the in-vitro conversion of epidermal cells into neurons by dedifferentiation of the epidermal basal cells followed by supplying the cells with the appropriate molecular factors for transdifferentiation. Specifically, the methods of the present invention involve dedifferentiation of epidermal cells in a calcium free growth media, expression of bHLH and/or Zn-finger neurogenic genes and inhibition of negative regulators of neuronal differentiation in the dedifferentiated epidermal cells. This methodology results in the conversion, or transdifferentiation, of these epidermal cells into viable neurons. Once created, these transdifferentiated neurons can be transplanted in, and/or grafted to, a patient in need for use in either cell therapies or gene therapies approaches. Advantageously, these newly created neurons can be used directly without requiring a step for cell expansion.

II. Experimental Basis of the Invention

The transdifferentiation process of the present invention involves the following basic steps:

1. Isolation of proliferating epidermal basal cells from the skin of a patient in need;
2. Dedifferentiation of epidermal basal cells in calcium free growth media;
3. Expression of neurogenic basic-Helix-Loop-Helix (NeuroD1, NeuroD2, ASH1) and/or Zn-finger (Zic3, MyT1) transcription factors with simultaneous suppression of the expression of homeobox genes MSX1 and bHLH transcription factor HES1 in epidermal basal cells; and
4. Growing cells resulting from step 3 (cells which over-express neurogenic transcription factors and have suppressed expression of MXS1 and HES1) in the presence of low concentrations of all-trans retinoic acid and various neurotrophins, such as, BDNF, NGF, NT-3, and NT-4.

In the first step of the invention, epidermal or skin cells are obtained from a patient in need. These epidermal cells are obtained or isolated via any type of surgical procedure. Preferably, these isolated cells are epidermal basal cells obtained from the skin of a patient. However, epithelial, or any other type of basal cell or proliferating cell population, can be used for the conversion of these cells into neurons.

In the second step of the inventive process, preferentially epidermal basal cells are dedifferentiated in a calcium free growth medium. This step involves treatment of the cells obtained in step one so that the cells lose the majority of differentiation specific gene expression to become dedifferentiated, that is, more primitive or developmentally less advanced. The dedifferentiation process is significant in that it allows for reprogramming of the neuronal development pathway. Since calcium ions are required to support development of keratinocytes (skin cells) from basal cells, removal of calcium results in dedifferentiation of basal cells. In other proliferating cell types, however, calcium may not be necessary to support development of any particular developmental pathway that is being deregulated. Other means to achieve the desired end of dedifferentiation involve treating the cells with specific growth factor or cytokines. Also, altering the specific gene expression pathway that is responsible for differentiation of epidermal cells by genetic manipulation may be used instead of eliminating calcium in the growth media. Moreover, elimination of calcium may not be required if other than proliferating epidermal basal cells are used.

In the third step, the invention utilizes molecular manipulation techniques to alter the cell differentiation pathway of epidermal cells. This alteration is accomplished by allowing for the expression of neurogenic transcription factors, such as the basic-Helix-Loop-Helix factors, Neuro D1, Neuro D2, or ASH1, and/or zinc-finger transcription factors, such as Zic3 or MyT1, while simultaneously, or near simultaneously, suppressing the expression of genes responsible for suppression of the neuronal development pathway, such as the basic-Helix-Loop-Helix factor HES1 and/or the homeobox factor MSX1. In addition to these genes, any other set of neurogenic and anti-neurogenic genes can be manipulated so as to achieve the desired end of transdifferentiation of epidermal cells or other proliferating cell types. Manipulations that can be used in this step of the inventive process include the use of variety of gene transfer protocols, such as microinjection of expression constructs, and a variety of DNA transfection techniques (such as, lipofections, liposomes, coprecipitation techniques, and different carriers), and viruses. Also protein transfer methods can be used to transiently express neurogenic transcription factors in the proliferating dedifferentiated cells.

Finally, in the fourth step of the invention, the transdifferentiated cells are preferably grown in the presence of a retinoid, such as all trans retinoic acid or vitamin A derivatives. In addition, neurotrophins or cytokines, such as BDNF, NGF, NT-3, NT-4, IL-6, can be used to obtain a substantial population of transdifferentiated neuronal cells. This step is optional in that it is not required for transdifferentiation. However, treatment with a retinoid and at least one neurotrophin increases the number of cells obtained.

The invention will now be described in greater detail by reference to the following non-limiting examples.

EXAMPLE I

Preparation of Epidermal Cell Culture and Dedifferentiation

Human adult skin was obtained from surgery procedures or skin biopsy. Before cultivation, as much as possible of the subepidermal tissue was removed by gentle scraping. Primary cultures were initiated by culturing 4–10 2×2 mm explants/35 mm tissue culture dish in Dulbecco's modified Eagle medium (GIBCO-BRL, Life Technologies, Inc.) with 15% fetal calf serum (GIBCO-BRL, Life Technologies, Inc.), 0.4 μg/ml hydrocortisone, and 10 ng/ml epidermal growth factor (Collaborative Research, Inc.). The medium was changed every three days. Thirty to thirty-five day old cultures were used for subsequent experimentation. Before transfections and further treatment, differentiated cell layers were stripped off by incubating the cultures in $Ca^{2+}$-free minimal essential medium (GIBCO-BRL, Life Technologies, Inc.). Generally, a calcium free media contains less than $10^{-6}$ M $Ca^{2+}$ ions. After 72 hours, suprabasal layers were detached and removed after shaking of the culture dish. This calcium free treatment also dedifferentiates epidermal basal cells, as they loose expression of cytokeratines which are characteristic of epidermal cells. The cultures were then refed medium with normal $Ca^{2+}$ concentration, that is, 2 mM calcium ions containing all the additives, that is, FCS (15%), hydrocortisone (0.4 μg/ml), EGF (10 ng/ml), and cultured 18–24 hours at 37° C. in an atmosphere containing 5% $CO_2$.

EXAMPLE II

Transfections of Cultured Epidermal Cells

Epidermal basal cells were transfected using a Ca-coprecipitation protocol (GIBCO-BRL, Life Technologies, Inc.), Lipofectamine reagent (GIBCO-BRL, Life Technologies, Inc.), and immunoliposomes (Holmberg et al., 1994). Ca-coprecipitation and Lipofectamine reagent were used as indicated by manufacturer. Ten μg of either pRcCMVneo eukaryotic expression vector (Invitrogen) alone, or cloned pRcCMVneo vectors containing either β-galactosidase (CMV-β-gal), NeuroD1 (CMV-ND1), NeuroD2, (CMV-ND2), hASH1 (CMV-hASH1), Zic1 (CMV-Zic1), or hMyT1 (CMV-MyT1) cDNAs were used to transfect cells in one 35 mm tissue culture dish. All the cDNAs were cloned in our laboratory using sequence information from Genebank: Accession numbers: hNeuroD1 D82347, U50822; hNeuroD2 U58681(SEQ ID NOS.: 1 and 7); (SEQ ID NOS.: 2 and 8) (SEQ ID NOS.: 3 and 9); hASH1 L08424(SEQ ID NOS.: 4 and 10); hzic1 D76435 (SEQ ID NOS.: 5 and 11); hMyT1 M96980(SEQ ID NOS. 6 and 12). All of the cloned genes were of human origin.

Oligonucleotide primers were designed based on the sequences of interest and used to amplify full length cDNAs using RT-PCR techniques and human fetal brain mRNA as a template. Also, NeuroD1, NeuroD2 and hASH1 cDNAs were isolated by screening the human fetal brain cDNA library (Stratagene). All cDNA sequences were verified by sequencing and in-vitro translation using reticulocyte lysate an in-vitro translation system (Amersham).

EXAMPLE III

Preparation and Use of Antisense Oligonucleotides

Human MSX1 antisense oligonucleotides sequences 1) 5'-GACACCGAGTGGCAAAGAAGTCATGTC (first methionine) (MSX1-1SEQ ID NO.: 13); and 2) 5'-CGGCTTCCTGTGGTCGGCCATGAG (third methionine) (MSX1-2SEQ ID NOS.: 14) were synthesized. Additionally, human full length HES1 cDNA from the human fetal brain cDNA library was isolated and sequenced (Stratagene). Two antisense oligonucleotides corresponding to the human HES1 open reading frame 5' sequence 1) 5'-ACCGGGGACGAGGAATTTTTCTCCATTATATCAGC (HES1-1SEQ ID NO: 15) and middle sequence 2) 5'-CACGGAGGTGCCGCTGTTGCTGGGCTGGTGT GGTGTAGAC (HES1-2SEQ ID NOS.: 16) were synthesized. The preferred antisense oligonucleotides are thio-modified by known methods. Therefore, thio-modified oligonucleotides corresponding to human MSX1 and human HES1 were synthesized and used to increase the stability of oligunucleotides in the culture media and in the cells. In the experimental protocol, described below, oligonucleotides were directly added to the culture media at the concentration of 5–10 μM. Randomly synthesized oligonucleotides and oligonucleotides corresponding to the sequence of human albumin were used as controls.

EXAMPLE IV

Analytical Method to Detect Transdifferentiation

Immunohistochemical detection of neurofilament M expression was chosen as one marker for neuronal differentiation. Cells were fixed with 4% paraformaldehyde and processed according to the immunohistochemical detection protocol recommended by the antibody manufacturer (Sigma, Inc.). Neurofilament M positive cells were counted by fluorescent microscopy. Several additional antibodies to neuronal antigens were used to characterize, in more detail, the nature of basal cell transdifferentiation into neurons. Antibodies against neural specific tubulin (Sigma, Inc.), neural specific enolase (Incstar, Inc.), microtubule associated protein 2 (MAP2, Boelringer Mannheim), and neurofilaments Mix (Stemberger) were used as recommended by the antibody manufacturer. Antibodies against glial fibrillary acidic protein (GFAP, Incstar) were used to detect differentiation of astrocytes from epidermal basal cells. Additionally, morphological criteria were used to detect transdifferention of epidermal basal cells into neuronal cells. Cells with neurites, or processes, longer than three cell diameters (50 microns or longer), and expressing at least one neuronal marker (antigen), were counted as neurons.

EXAMPLE V

Transdifferentiation Protocol and Experimental Results

Various combinations of neural regulators leading to expression, or over-expression, of neurogenic bHLH and/or Zn-finger transcription factors and substantially simultaneous suppression of MSX1 and/or HES1 expression were tested to ascertain their effect on transdifferentiation of epidermal basal cells. Results of these experiments are presented in Table 1.

For these experiments, a immunoliposome transfection method is preferred, since it resulted in the highest transfection efficiency. Other methods of transfection that yield high transfection efficiency, such as Ca-coprecipitation, Lipofectamine, or Fugene-6 (Boehringer Mannheim, Inc.), known in the art, can be used instead of immunoliposomes. After transfection and antisense oligonucleotide treatments, cells were grown in the presence of all-trans retinoic acid ($10^{-7}$M) and BDNF (20 ng/ml) for 5 days before immunostaining.

Table 1 shows the results of the transdifferentiation procedures described above leading to the conversion of epidermal basal cells into neuronal cells in-vitro. Various combinations of simultaneous expression, or near simultaneous expression, of neurogenic bHLH and/or Zn-finger transcription factors and suppression of expression of MSX1 and/or HES1 genes were used to initiate transdifferentiation. Neurofilament M immunostaining and evaluation of the length of neurites, or processes (50 microns or longer were counted as neurites) were used to identify neuronal cells. Controls using pRCMV vector plasmid and randomly synthesized oligonucleotides, and oligonucleotides corresponding to the sequence of human albumin, showed no transdifferentiation of epidermal basal cells.

TABLE I

TRANSDIFFERENTIATION OF EPIDERMAL CELLS

| TREATMENT | % NEURONAL CELLS |
|---|---|
| control, no treatment: | 0 |
| Over-expression: | |
| NeuroD1 | 0.01 |
| NeuroD2 | 0.03 |
| ASH1 | 0 |
| Zic1 | 0 |
| MyT1 | 0 |
| NeuroD1 + Zic1 | 0.04 |
| NeuroD2 + Zic1 | 0.05 |
| NeuroD1 + NeuroD2 + Zic1 | 0.05 |
| NeuroD1 + MyT1 | 0.02 |
| NeuroD2 + MyT1 | 0.03 |
| NeuroD1 + NeuroD2 + MyT1 | 0.05 |
| NeuroD1 + NeuroD2 + MyT1 + Zic1 | 0.05 |
| Antisense oligonucleotides: | |
| MSX1-1 | 0 |
| MSX1-2 | 0 |
| HES1-1 | 0 |
| HES1-2 | 0 |
| MSX1-1 + MSX1-2 + HES1-1 + HES1-2 | 0 |
| Combination of antisense oligonucleotides and over-expression of neurogenic factors: | |
| NeuroD1 + NeuroD2 + MSX1-1 + MSX1-2 | 0.5 |
| NeuroD1 + NeuroD2 + HES1-1 + HES1-2 | 0.8 |
| NeuroD1 + NeuroD2 + MSX1-1 + HES1-1 | 7 |
| Zic1 + MSX1-1 + MSX1-2 | 0.05 |
| Zic1 + HES1-1 + HES1-2 | 3 |
| MyT1 + MSX1-1 + MSX1-2 | 0.01 |
| MyT1 + HES1-1 + HES1-2 | 0.5 |
| MyT1 + MSX1-1 + HES1-1 | 0.9 |
| NeuroD1 + Zic1 + MSX1-1 | 11 |

TABLE I-continued

TRANSDIFFERENTIATION OF EPIDERMAL CELLS

| TREATMENT | % NEURONAL CELLS |
|---|---|
| NeuroD1 + Zic1 + MSX1-1 + HES1-1 | 20 |
| NeuroD1 + MyT1 + MSX1-1 | 10 |
| NeuroD1 + MyT1 + MSX1-1 + HES1-1 | 26 |
| NeuroD1 + Zic1 + MyT1 + MSX1-1 + HES1-1 | 25 |

In summary, transdifferentiation of epidermal cells into neurons is best achieved by the combined effect of expressing neurogenic transcription factors, which positively regulate neuronal differentiation, and antisense oligonucleotides, corresponding to negative regulators of neuronal differentiation. The experimental data indicate that a preferred method of transdifferentiation of epidermal cells into neurons includes the expression of both a bHLH and zinc finger transcription factor, which positively regulate neuronal differentiation, in the presence of at least one antisense DNA, corresponding to a negative regulator of epidermal differentiation. Additionally, the expression of two bHLH transcription factors in the presence of two negative regulator antisense DNAs yielded a fairly high percentage of differentiated neurons.

EXAMPLE VI

Characterization of the Transdifferentiated Neuronal Cells

To further evaluate the transdifferention process and nature of newly formed neuronal cells, expression of several neuronal marker genes in these cells using immunostaining with specific antibodies against neuronal marker proteins were analyzed. In these experiments, the following combinations of transfection of neurogenic genes and antisense oligonucleotide treatments were used:

NeuroD1+Zic1+MSX1-1+HES1-1
NeuroD1+MyT1+MSX1-1+HES1-1
NeuroD1+Zic1+MyT1+MSX1-1+HES1-1

The results of these experiments show that Neurofilament M positive transdifferentiated cells also express neural specific tubulin, neural specific enolase, and microtubule associated protein 2. Expression of a number of neuronal antigens and morphological changes (neurites 50 microns or longer) of transdifferentiated cells shows that the procedure of transdifferention results in normal and viable neuronal cells that can be used in cell therapy applications. Moroever, the newly formed neuronal cells of the present invention have the morphological and functional criteria of neurons: they develop long neurites with a growth cones at the end, they express a number of neural specific genes, and they do not continue to proliferate in conditions which induce differentiation, such as, in the presence of all-trans retinoic acid ($10^{-7}$M) and BDNF (20 ng/ml).

Finally, staining of treated epidermal cell cultures with antibodies against glial fibrillary acidic protein shows that small percentage (around 5%) of cells also express GFAP. This is an indication that transdifferentiated cells acquire characteristics of astroglial cells, either directly or indirectly. One possible explanation is that expression of neurogenic genes and blocking expression of inhibitors of neurogenesis results in formation of neuronal progenitor cells that differentiate both neurons and astroglial cells in vitro.

III. Clinical and Research Applications of the Invention

The technology of the present invention can be developed for direct application to many aspects of cell therapy and genetically-based drug delivery systems used to treat nervous system disorders and diseases. Outlined below are several areas of application of the present invention.

The characteristics and properties of the transdifferentiated neurons of the present invention make these newly created neurons viable as a fundamental biotechnology tool directed to the human nervous system. Moreover, the transdifferentiated neurons of the invention meet the technical criteria for use in cell and gene therapies directed to nervous system disease and disorders. First, the transdifferentiated neurons display the morphological and functional features of neurons: they develop long neurites with a growth cones at the end, they express a number of neural specific genes, and they do not continue to proliferate in conditions which induce differentiation. Therefore, for use in gene therapy and cell therapy, the newly created neuronal cells can not only deliver a single potential gene or factor, but additionally are capable of furnishing the whole infrastructure for nerve regeneration.

Second, the cultured transdifferentiated cells can be propagated as multipotential nervous system progenitor cells in conditions that favor proliferation and do not induce differentiation. Hence, these progenitor cells retain the capacity to become many different types of neurons depending upon the environmental cues to which they are exposed. For example, treating newly formed neuronal cells plated on laminin coated surface with all-trans retinoic acid ($10^{-7}$ M) and BDNF (10 ng/ml) for 5–15 days results in development of GABAergic neurons, whereas treatment with glial conditioned media and sonic hedgehog aminoterminal peptide results in development of mostly dopaminergic neurons. This broad plasticity suggests that, once transplanted, the cells of the present invention will retain the capacity to conform to many different host brain regions and to differentiate into neurons specific for that particular host region. These intrinsic properties of the transdifferentiated neurons are different from the existing tumorigenic cell lines, where some neuronal differentiation can be induced under artificial conditions.

Third, another advantage of these transdifferentiated neurons, is that there is no need for cell expansion, as is required with stem cell technology used to generate neurons for cell and gene therapies. Thus, the newly created neurons of the present invention are sufficient in number (several millions of cells) for direct transplantation. In summary, the unique characteristics and properties of these transdifferentiated neurons yield an invention of potentially significant scientific and commercial potential.

1. Gene Therapy Approaches
   a) Parkinson's Disease

Parkinson's Disease results mainly from degeneration of dopamine releasing neurons in the substantia nigra of the brain and the resulting depletion of dopamine neurotransmitter in the striatum. The cause of this degeneration is unknown, but the motor degeneration symptoms of the disease can be alleviated by peripherally administering the dopamine precursor, L-dopa, at the early onset of the disease. As the disease continues to worsen, L-dopa is no longer effective, and currently, no further treatment is available. One promising treatment being developed is to transplant dopamine-rich substantia nigra neurons from fetal brain into the striatum of the brain of the patient. Results obtained from various clinical studies look extremely optimistic, however, it is estimated that up to 10 fetal brains are needed to obtain a sufficient number of cells for one transplant operation. This requirement renders unfeasible the wide application of the transplantation of primary fetal neurons as a therapeutic treatment modality. This problem is resolved, however, by utilizing the transdifferentiated neuronal cells of the present invention for treatment of Parkinson's disease.

EXAMPLE VII

A Gene Therapy Application for Transdifferentiated Neuronal Cells in Parkinson's Disease It is now widely recognized that transplantation of dopamine producing cells is the most promising therapy of treating severe Parkinson's disease. Stable cell populations or cell lines genetically engineered to produce dopamine is essential to an effective therapy. Since tyrosine hydroxylase (TH) is the key enzyme for dopamine synthesis, cloning this gene in an appropriate expression vector is a first step in the method of treatment. Thus, human TH cDNA will be cloned into eukaryotic expression vector under the control of neuronal specific promoter (for example, neurofilament, neural specific enolase). Expression constructs will be transfected into epidermal basal cells of a patient, using high efficiency transfection protocols (Lipofectamine, Ca-coprecipiotation etc.), followed by selection of the clones which demonstrate stable integration of the expression vector. These clones will be used for transdifferentiation procedures to obtain newly formed neurons that express TH. Thus, human neurons derived from transdifferentiated cells of the present invention will be produced which express the tyrosine hydroxylase (TH) gene. These cells will be transplanted into the patient's striatum or brain. First, the cells will be implanted bilaterally in the caudate nucleus and putamen by using Magnetic Resonance Imaging (MRI)-guided stereotactic teclniques. The stereotactic frame will be fixed to the skull after administration of local anesthesia. The caudate nucleus and putamen then will be visualized with MRI. Thereafter, under general anesthesia, ten passes with very thin stereotactic needles will be made bilaterally, 4 mm apart in the caudate and putamen. The rationale for track spacing at approximately 4 mm intervals is important because fetal dopamine neuron processes grow several millimeters, reinnervating the host's striatum. Four trajectories for needle tracks in the caudate and six tracks in the putamen will be calculated to avoid the posterior limb of the internal capsule. The entry points for the putamen and caudate tracks will be at two different sites on the surface of the brain. The tracks to the putamen will be approximately vertical with reference to a coronal plane, while the approach to the caudate will be at an angle of approximately 30 degrees.

b) Nerve Growth Factors

The transdifferentiated neuronal cells of the present invention can be transfected with nerve growth factors of potential interest. Primary examples of growth factors currently in clinical trials or under full development by various companies are listed below in Table II. So far, tests of the effects of growth factors on the brain and nervous system have been limited to direct peripheral injection of large doses of these factors, which carries a significant risk of side effects, since most growth factors affect many different populations of neurons and non-neural tissues. These problems can be overcome by generating transdifferentiated neuronal cell lines that stably express these growth factors and secrete the growth factors after transplantation.

TABLE II

NEUROTROPIC FACTORS AND DISEASES

| NEUROTROPIC FACTOR | DISEASE |
|---|---|
| Nerve growth factor | Alzheimer's Disease |
| | Diabetic neuropathy |
| | Taxol neuropathy |
| | Compressive neuropathy |
| | AIDS-related neuropathy |
| Brain-derived growth factor | Amyotrophic lateral sclerosis |
| Neurotrophin 3 | Large fiber neuropathy |
| Insulin-like growth factor | Amyotrophic lateral sclerosis |
| | Vincristine neuropathy |
| | Taxol neuropathy |
| Ciliary neurotrophic factor | Amyotrophic lateral sclerosis |
| Glia-derived neurotrophic factor | Parkinson's Disease |

EXAMPLE VIII

A Gene Therapy Application for Transdifferentiated Neuronal Cells for the Delivery of Nerve Growth Factors to the Brain Local delivery of neurotrophic factors has been suggested as a method to treat several neurological conditions (see Table II). Transdifferentiated epidermal cells from patients own skin represent a vehicle for neurotrophic factor delivery. Human neurotrophic factors cDNAs will be cloned into eukaryotic expression vector under the control of neuronal specific promoter (for example, neurofilament or neural specific enolase). Expression constructs will be transfected into epidermal basal cells using high efficiency transfection protocols (Lipofectamine, Ca-coprecipiotation etc.). This procedure is followed by selection of the clones that demonstrate stable integration of expression vector. These clones will then be used for transdifferentiation procedures to obtain newly formed neurons that express particular neurotrophic factors at significantly high levels. Neuronal cells that express these neurotrophic factors will be transplanted into the patients brain and/or nervous system, as described in Example VII, into locations which are in need of neurotrophic factor delivery.

2. Cell Therapy Approaches

In most neurological diseases, unlike Parkinson's Disease, the underlying cause of symptoms cannot be attributed to a single factor. This condition renders the therapeutic approach of introducing a single gene by gene therapy or single neuronal type replacement by cell therapy ineffective. Rather, replacement of the lost, or diseased, host neuronal cells, or even neuronal networks, by healthy cells and neuronal networks is required. The present invention enables us to develop different types of neurons from a patient's own epidermal basal cells. These newly formed neurons can be cultured separately, or together, to stimulate formation of functional neuronal networks that can be used for replacement therapies. Alternatively, different types of neurons can be transplanted and induced to form functional connections between themselves and host neurons, in situ, in the brain or in the spinal cord. Ability to differentiate de novo, formed neurons into variety of neuronal types in vitro and in vivo makes this approach especially powerful and useful for replacement of complex strictures and networks in the nervous system.

EXAMPLE IX

A Cell Therapy Application for Transdifferentiated Neuronal Cells as a Treatment for Neurotraumas, Stroke and Neurodegenerative Disease As an example for restoring local circuitry in the nervous system is the formation of a functional "pattern generator"

in the injured spinal cord. Several data demonstrate that a pattern generator functions in humans, and moreover, that physical therapy can stimulate stepping and use of legs in spinal cord injury patients. (For a review, see Wickelgren, 1998). The pattern generator involves different types of interneurons that connect sensory afferents and motorneurons. Transdifferentiated epidermal basal cells will be treated so as to form all major neuronal cell types that are required for functioning of pattern generator. Here cells will be mixed together wherein natural synapse formation will occur. Since pattern generators are composed of major excitatory (glutamatergic, cholinergic) and inhibitory (glycinergic including Renshaw cells, GABAergic) neurons, first, these neuronal types will be generated by the methods of the present invention described above. Second, excitatory and inhibitory neurons produced in the first step will be grown in co-cultures to stimulate formation of functional connections between the neuron cells. This step will yield aggregates of cells which will be transplanted into the injured spinal cord of a patient. An alternative approach will be to develop different neuronal cell types separately, and mix these before transplantation into the spinal cord. By use of these procedures which permits the transplantation of a large number of different excitatory and inhibitory neurons, a functional set of neuronal connections, capable of supporting local functions of the spinal cord will be developed.

3. Search for Novel Growth Factors

One of the central principles of modern neurobiology is that each of the major projection neurons, if not all neurons, requires specific signals (trophic factors) to reach their target cells and survive. Neuropathies in many diseases may be caused by, or involve lack of, such growth factors. These growth factors represent the next generation of preventative and therapeutic drugs for nervous system disorders, and hence the enormous capitalization has been invested in the search and development of novel growth factors by the biotechnology industry.

Implicit in the observation that mature neurons can be produced from transdifferentiated neurons is the fact that various growth factors can be tested using these cells to assay for final determination of cell types, maturation, and continued support of cell survival. Most of the growth factors known so far in the nervous system were discovered by their effects on peripheral nerves and these most likely represent a very minor fraction of existing growth factors in the brain.

Search for growth factors from the brain has been difficult mainly because particular neuronal cell types are difficult to isolate from the brain and maintain in defined culture conditions. The use of transdifferentiated epidermal cells overcomes this problem and opens new assays to screen potential growth factors.

EXAMPLE X

Use of Transdifferentiated Neuronal Cells as a Research Tool in the Search for Novel Growth Factors The different types of neuronal cells that are created from transdifferentiated epidermal basal cells provides a novel research tool for the discovery and analyses of the effect of new, and also already characterized, growth/neurotrophic factors. Epidermal basal cells will be transdifferentiated into different types of neuronal cells characterized by a particular subtype of neurons. These specific neuronal cells will be used to test, or assay, the effect of potential growth factor sources (tissue homogenates, expression cDNA library products, etc.) on the survival and functional characteristics of cells. For example, cell number will be counted for the analysis of survival of neuronal cells after exposure to growth factors. A wide spectrum of experimental analyses of the functional characteristics of these neurons, known in the art, can be performed to assay the effect of these novel growth factors on the newly created neurons. Experimental techniques, based on an electrophysiological characteristic (patch clamp, different types of intracellular recording, etc.) and molecular biological (gene expression profiles, organization of cytoskeleton, organization of ion channels and receptors etc.) will be used to detect effects of potential growth/neurotrophic factors on particular cell types.

4. Assays for Drug Screening

As more and more neurotransmitter receptors and signal transducing proteins are being identified from the brain, it is becoming clear that the dogma of one neurotransmitter activating one receptor is an over-simplification. Most receptor complexes in neurons are composed of protein subunits encoded by several genes and each gene synthesizes many different variations of the protein. These variations result in a wide range of possible receptor combinations, and not a single receptor that can interact with a neurotransmitter. Consequently, a range of signal output may be produced by a single neurotransmitter action. The specific signal effected by a neurotransmitter on a neuron, then, depends on which receptor complex is produced by the cell. Thus, cellular diversity must parallel the molecular diversity and constitute a major structural element underlying the complexity of brain function.

Drug discovery by traditional pharmacology had been performed without the knowledge of such complexity using whole brain homogenate and animals. These studies mostly produced analogs of neurotransmitters with broad actions and side effects. The next generation of pharmaceutical drugs aimed at modifying specific brain functions may be obtained by screening potential chemicals against neurons displaying a specific profile of neurotransmitters, receptors complexes, and ion channels.

Epidermal basal cells transdifferentiated into neurons in culture can express several neurotransmitters and receptor complexes. Cell lines derived from these cells can be developed which, when differentiated into mature neurons, would display a unique profile of neurotransmitter receptor complexes. Such neuronal cell lines will be valuable tools for designing and screening potential drugs.

EXAMPLE XI

Use of Transdifferentiated Neuronal Cells as a Research Tool in Drug Screening

Different types of neuronal cells created from transdifferentiated epidermal basal cells of the present invention will provide novel methodologies to screen potential drugs. For example, using the epidermal basal cells from patients with genetic defects that affect nervous system will make it possible to create various types of neuronal cells which also carry this genetic defect. These cells will be used for screening of drugs which potentially have effect on the diseased neurons. Epidermal basal cells will be transdifferentiated into various types of neuronal cells with characteristics of the desired subtype of neurons. These specific neuronal cells will be used to test, or assay, the effect of potential drugs on the survival and functional characteristics of the cells. Cell number will be counted for the analysis of survival of neuronal cells after exposure to drugs. A wide spectrum of electrophysiological (patch clamp, different types of intracellular recording etc.) and molecular biological (gene expression profiles, organization of cytoskeleton, organization of ion channels and receptors etc.) techniques can be used to detect effects of potential drugs on particular cell types.

In summary, the transdifferentiation nerve cell technology of the present invention offers broad and significant potentials for treating nervous system disorders in both the areas of cell and gene therapy, as well as offering a potential new source of human neurons for research and drug screening.

The following scientific articles have been cited in this application.

Bellefroid, E. J., Bourguignon, C., Hollemann, T., Ma, Q., Anderson, D. J., Kintner, C. and Pieler, T. 1996. X-MyT1, a Xenopus C2HC-type zinc finger protein with a regulatory function in neuronal differentiation. *Cell* 87, 1191–1202.

Ishibashi, M., Moriyoshi, K., Sasai, Y., Shiota, K., Nakanishi, and S., Kageyama, R. 1994. Persistent expression of helix-loop-helix factor HES-1 prevents mammalian neuronal differentiation in the central nervous system. *EMBO J*. 13, 1799–1805.

Ishibashi, M., Ang, S.-L., Shiota, K., Nakanishi, S., Kageyama, R. and Guillemot, F. (1995). Targeted disruption of mammalian hairy and Enhancer of split homolog-1 (HES-1) leads to up-regulation to neuronal helix-loop-helix factors, and severe neural tube defects. *Genes & Dev.* 9, 3136–3148.

Lee, J. E., Hollenberg, S. M., Snider, L., Turner, D. L., Lipnick, N. and Weintraub, H. (1995). Conversion of Xenopus ectoderm into neurons by neuroD, a basic helix-loop-helix protein. *Science* 268, 836–844.

Ma, Q., Kintner, C. and Anderson, D. J. (1996). Identification of neurogenein, a vertebrate neuronal determination gene. *Cell* 87, 43–52.

McCormick, M. B., Tamimi, R. M., Snider, L., Asakura, A., Bergstrom, D. and Tapscott, S. J. (1996). NeuroD2 and NeuroD3: distinct expression patterns and transcriptional activation potentials within the neuroD gene family. *Mol. Cell. Biol.* 16, 5792–5800.

Nakata, K., Nagai, T., Aruga, J. and Mikoshiba, K. 1997. Xenopus Zic3, a primary regulator both in neuronal and neuronal crest development. *Proc. Natl. Acad. Sci. USA* 94, 11980–11985.

Suzuki, A., Ueno, N., Hemmati-Bivenlou, A. 1997. Xenopus msx1 mediates epidermal induction and neuronal inhibition by BMP4. *Development* 124, 3037–3044.

Tanabe, Y. And Jessell, T. M. 1996. Diversity and pattern in the developing spinal cord. *Science* 274, 1115–1123.

Wickelgren, I. 1998. Teaching the spinal cord to walk. Research News. *Science* 279, 319–321.

All scientific articles cited herein are hereby incorporated by reference in their entirety and relied upon for their scientific import.

While the invention can be described in connection with what is presently considered to be the most practical and preferred embodiments, it is to be understood that the invention is not limited to the disclosed embodiments, but on the contrary is intended to cover various modifications and equivalent arrangements included within the spirit and scope of the description of the invention and the appended claims. Thus, it is to be understood that variations in the present invention can be made without departing from the novel aspects of this invention as described in the specification and defined in the claims.

We claim:

1. A method of transdifferentiating an epidermal basal cell into a cell having a morphological, physiological and/or immunological feature of a viable neuronal cell, comprising the steps of:

(a) obtaining an epidermal basal cell from a proliferating epidermal basal cell population derived from a patient's skin;

(b) transfecting said epidermal basal cell, in vitro, with one or more eukaryotic expression vector(s) containing at least one cDNA encoding a human neurogenic transcription factor, or homologous non-human counterpart, from the group consisting of NeuroD1, NeuroD2, ASH1, Zic1, Zic3, and MyT1, such that at least one of the neurogenic transcription factor(s) is expressed in said cell;

(c) adding at least one antisense oligonucleotide comprising a segment of a human MSX1 gene or human HES1 gene, or homologous non-human counterpart of either of these, to an in vitro growth medium, thereby suppressing at least one negative regulator of neuronal differentiation; and (d) growing the transfected epidermal cell with a retinoid and at least one neurotrophin from the group consisting of BDNF, NGF, NT-3, and NT-4, or a cytokine comprising IL-6, whereby said epidermal cell is transdifferentiated into a cell that comprises one or more morphological neurite-like processes at least about 50 micrometers in length and expresses at least one neural-specific antigen selected from the group consisting of neurofilament M, neural-specific tubulin, neural-specific enolase, and microtubule associated protein 2.

2. The method of claim 1, wherein the eukaryotic expression vector(s) of the transfection step comprise a CMV promoter sequence operatively linked to a DNA(s) encoding the neurogenic transgenic transcription factor from the group consisting of NeuroD1, NeuroD2, ASH1, Zic1, Zic3, and MyT1, and wherein the DNA encoding the neurogenic transcription factor is of human origin or is a homologous non-human counterpart of a gene encoding any of these.

3. A transdifferentiated cell having a morphological, physiolooical and/or immunological feature of a viable neuronal cell, comprising:

an epidermal basal cell transfected with one or more expression vectors comprising a CMV promoter sequence operatively linked to a DNA(s) encoding the neurogenic transcription factor NeuroD1, NeuroD2, ASH1, Zic1, Zic3, or MyT1, wherein the DNA encoding the neurogenic transcription factor is of human origin, or is a non-human homologous counterpart or a gene encoding any of these, wherein said cell is treated with at least one antisense oligonucleotide comprising a segment(s) of human MSX1 gene or human HES1 gene, or non-human homologous counterpart thereof, and wherein said cell was grown in the presence of a retinoid and at least one neurotrophin, thereby transdifferentiating said epidermal cell into a cell comprising one or more morphological neurite-like process(es) at least about 50 micrometers in length and expressing at least one neural-specific antigen selected from the group consisting of neurofilament M, neural-specific tubulin, neural-specific enolase, and microtubule associated protein 2.

4. A transdifferentiated cell having a morphological, physiological and/or immunological feature of a viable neuronal cell produced by the process of claim 1.

5. A kit for converting epidermal basal cells to cells that comprise one or more morphological neurite-like processes at least about 50 micrometers in length and express at least one neural-specific antigen selected from the group consisting of neurofilament M, neural-specific tubulin, neural-specific enolase, and microtubule associated protein 2, said kit comprising:

one or more eukaryotic expression vector(s) containing cDNA encoding a neurogenic transcription factor, or fragment thereof, from the group consisting of NeuroD1, NeuroD2, ASH1, Zic1, Zic3, and MyT1, or a non-human homologous counterpart of any of these;

at least one antisense oligonucleotide corresponding to the human MSX1 gene, the human HES1 gene, or a non-human homologous counterpart of either of these;

a retinoid and at least one neurotrophin from the group consisting of BDNF, NGF, NT-3, and NT-4.

6. The kit of claim 5, further comprising instruction for use with a patient's claims 24–26 are canceled.

7. A method of using transdifferentiated epidermal basal cells having a morphological, physiological and/or immunological feature of viable neuronal cells to isolate a novel nerve growth factor comprising the steps of:

(a) transdifferentiating epidermal basal cells to cells having a morphological, physiological and/or immunological feature of a viable neuronal cell as in claim 1;

(b) culturing the transdifferentiated cells in vitro;

(c) exposing the cultured cells in vitro, to a potential nerve growth factor; and (d) detecting the presence or absence of an effect of the potential nerve growth factor on the survival of the cells or on a morphological or electrophysiolocical characteristic and/or molecular biological property of said transdifferentiated epidermal basal cells, whereby an effect altering cell survival, a morphological or electrophysiological characteristic and/or a molecular biological property of the cells indicates the activity of the novel nerve growth factor.

8. A method of using transdifferentiated epidermal basal cells having a morphological, physiological and/or immunological feature of viable neuronal cells to screen a potential new drug to treat a nervous system disorder comprising the steps of:

(a) transdifferentiating epidermal basal cells from a patient with a nervous system disorder to cells having a morphological, physiological and/or immunological feature of a viable neuronal cell as in claim 1;

(b) culturing the transdifferentiated cells in vitro;

(c) exposing the cultured cells, in vitro, to a potential new drug; and (d) detecting the presence or absence of an effect of the potential new drug on the survival of the cells in vitro or on a morphological or electrophysiological characteristic and/or molecular biological property of said transdifferentiated epidermal basal cells, whereby an effect altering cell survival, a morphological or electrophysiological characteristic and/or a molecular biological property of the cells in vitro indicates the activity of the potential new drug.

9. A transdifferentiated epiderinal basal cell having a morphological, physiological and/or immunological feature of a viable neuronal cell comprising:

a cell of epidermal basal cell origin which displays one or more morphological neurite-like process(es) at least about 50 micrometers in length and expresses at least one neural-specific antigen selected from the group consisting of neurofilament M, neural-specific tubulin, neural-specific enolase, and microtubule associated protein 2.

10. The cell of claim 9, wherein the the cell further displays a lack of proliferation in conditions which induce differentiation.

11. The cell of claim 9, wherein the cell is GABAergic.

12. The cell of claim 9, wherein the cell is dopaminergic.

13. A transdifferentiated cell comprising a cell of basal epidermal origin which displays a morphological, physiological and/or immunological feature of an astroglial cell and wherein said immunological feature is expression of glial fibrillary acidic protein (GFAP).

14. The method of claim 1, wherein obtaining an epidermal basal cell comprises selecting basal cells from keratinocytes using a calcium-free medium.

15. The method of claim 1, wherein said antisense oligonucleotide(s) is modified with one or more thio groups.

* * * * *

UNITED STATES PATENT AND TRADEMARK OFFICE
CERTIFICATE OF CORRECTION

PATENT NO.    : 6,087,168
DATED         : July 11, 2000
INVENTOR(S)   : Levesque et al.

Page 1 of 1

It is certified that error appears in the above-identified patent and that said Letters Patent is hereby corrected as shown below:

<u>Column 45,</u>
Line 31, delete "physioloocial" and insert therefor -- physiological --.
Line 40, delete "or" after counterpart and insert therefor -- of --.

<u>Column 46,</u>
Line 10, delete "claims 24-26 are canceled." and insert therefor -- skin cells. --.
Line 26, delete "electrophysiolocical" and insert therefor -- electrophysiological --.
Line 57, delete "epiderinal" and insert therefor -- epidermal --.

Signed and Sealed this

Eighteenth Day of September, 2001

Attest:

NICHOLAS P. GODICI
Attesting Officer    Acting Director of the United States Patent and Trademark Office

```
                       SEQUENCE LISTING

<160> NUMBER OF SEQ ID NOS: 16

<210> SEQ ID NO 1
<211> LENGTH: 2502
<212> TYPE: DNA
<213> ORGANISM: Human
<220> FEATURE:
<221> NAME/KEY: gene
<222> LOCATION: (0)...(0)
<223> OTHER INFORMATION: Neuro D1 gene: Genbank accession D82347

<400> SEQUENCE: 1
cggccacgac acgaggaatt cgcccacgca ggaggcacgg cgtccggagg ccccagggtt      60
atgagactat cactgctcag gacctactaa caacaaagga aatcgaaaca tgaccaaatc     120
gtacagcgag agtgggctga tgggcgagcc tcagcccaa  ggtcctccaa gctggacaga     180
cgagtgtctc agttctcagg acgaggagca cgaggcagac aagaaggagg acgacctcga     240
agccatgaac gcagaggagg actcactgag gaacggggga gaggaggagg acgaagatga     300
ggacctggaa gaggaggaag aagaggaaga ggaggatgac gatcaaaagc caagagacg     360 cggccccaaa aagaagaaga tgactaaggc tcgcctggag cgttttaaat tgagacgcat     420
gaaggctaac gcccggagc ggaaccgcat gcacggactg aacgcggcgc tagacaacct     480
gcgcaaggtg gtgccttgct attctaagac gcagaagctg tccaaaatcg agactctgcg     540
cttggccaag aactacatct gggctctgtc ggagatcctg cgctcaggca aaagcccaga     600
cctggtctcc ttcgttcaga cgctttgcaa gggcttatcc caacccacca ccaacctggt     660
tgggggctgc ctgcaactca atcctcggac ttttctgcct gagcagaacc aggacatgcc     720
```

-continued

```
cccccacctg ccgacggcca gcgcttcctt ccctgtacac ccctactcct accagtcgcc      780
tgggctgccc agtccgcctt acggtaccat ggacagctcc catgtcttcc acgttaagcc      840
tccgccgcac gcctacagcg cagcgctgga gcccttcttt gaaagccctc tgactgattg      900
caccagccct tcctttgatg gacccctcag cccgccgctc agcatcaatg gcaacttctc      960
tttcaaacac gaaccgtccg ccgagtttga gaaaaattat gcctttacca tgcactatcc     1020
tgcagcgaca ctggcagggg cccaaagcca cggatcaatc ttctcaggca ccgctgcccc     1080
tcgctgcgag atccccatag acaatattat gtccttcgat agccattcac atcatgagcg     1140
agtcatgagt gcccagctca atgccatatt tcatgattag aggcacgcca gtttcaccat     1200
ttccgggaaa cgaacccact gtgcttacag tgactgtcgt gtttacaaaa ggcagccctt     1260
tgggtactac tgctgcaaag tgcaaatact ccaagcttca agtgatatat gtatttattg     1320
tcattactgc ctttggaaga aacaggggat caaagttcct gttcacctta tgtattattt     1380
tctatagctc ttctatttaa aaataaaaa aatacagtaa agtttaaaaa atacaccacg      1440
aatttggtgt ggctgtattc agatcgtatt aattatctga tcgggataac aaaatcacaa     1500
gcaataatta ggatctatgc aattttttaaa ctagtaatgg gccaattaaa atatatataa    1560
atatatattt ttcaaccagc attttactac ttgttacctt tcccatgctg aattattttg     1620
ttgtgatttt gtacagaatt tttaatgact ttttataatg tggatttcct attttaaaac     1680
catgcagctt catcaatttt tatacatatc agaaaagtag aattatatct aatttataca     1740
aaataattta actaatttaa accagcagaa aagtgcttag aaagttattg tgttgcctta     1800
gcacttcttt cctctccaat tgtaaaaaaa aaaaaaaaa aaaaaaaaaa aaaaaaattg      1860
cacaatttga gcaattcatt tcactttaaa gtctttccgt ctccctaaaa taaaaaccag     1920
aatcataatt ttcaagagga gaaaaaatta agagatacat tccctatcac aacatatcaa     1980
ttcaacacat tacttgcaca agcttgtata tacatattat aaatagatgc caacataccc     2040
ttctttaaat cacaagctgc ttgactatca catacaattt gcactgttac ttttttagtct    2100 tttactcctt tgcattccat gattttacag agaatctgaa gctattgatg tttccagaaa     2160
atataaatgc atgattttat acatagtcac ccccatggtg ggttgtcata tattcatgta     2220
ataaatctga gcctaaatct aatcaggttg ttaatgttgg gagttatatc tatagtagtc     2280
aattagtaca gtagcttaaa taaattcccc ccatttaatt cataattaga acaatagcta     2340
ttgcatgtaa aatgcagtcc agaataagtg ctgtttgaga tgtgatgctg gtaccactgg     2400
aatcgatctg tactgtaatt ttgtttgtaa tcctgtatat tatggtgtaa tgcacaattt     2460
agaaaacatt catccagttg caataaaata gtattgaaag tg                        2502
```

<210> SEQ ID NO 2
<211> LENGTH: 1676
<212> TYPE: DNA
<213> ORGANISM: Human
<220> FEATURE:
<221> NAME/KEY: gene
<222> LOCATION: (0)...(0)
<223> OTHER INFORMATION: Neurogenic helix-loop-helix protein (Neurod 1)
      gene
      Genbank accession J50822

<400> SEQUENCE: 2

```
acatcgatta acttttctc agaggcattc attttgtaat gggcaggtac ttttcgcaag       60
catttgtaca ggtttaggga gtggaagctg aaggcgatct ttcttttgat atagcgtttt     120
```

-continued

| | |
|---|---|
| tctgcttttc tttctgtttg cctctccctt gttgaatgta ggaaatcgaa acatgaccaa | 180 |
| atcgtacagc gagagtgggc tgatgggcga gcctcagccc caaggtcctc caagctggac | 240 |
| agacgagtgt ctcagttctc aggacgagga gcacgaggca gacaagaagg aggacgacct | 300 |
| cgaagccatg aacgcagagg aggactcact gaggaacggg ggagaggagg aggacgaaga | 360 |
| tgaggacctg gaagaggagg aagaagagga agaggaggat gacgatcaaa agcccaagag | 420 |
| acgcggcccc aaaaagaaga agatgactaa ggctcgcctg gagcgtttta aattgagacg | 480 |
| catgaaggct aacgcccggg agcggaaccg catgcacgga ctgaacgcgg cgctagacaa | 540 |
| cctgcgcaag gtggtgcctt gctattctaa gacgcagaag ctgtccaaaa tcgagactct | 600 |
| gcgcttggcc aagaactaca tctgggctct gtcggagatc tcgcgctcag gcaaaagccc | 660 |
| agacctggtc tccttcgttc agacgctttg caagggctta tcccaaccca ccaccaacct | 720 |
| ggttgcgggc tgcctgcaac tcaatcctcg acttttctg cctgagcaga accaggacat | 780 |
| gcccccgcac ctgccgacgg ccagcgcttc cttccctgta caccctact cctaccagtc | 840 |
| gcctgggctg cccagtccgc cttacggtac catggacagc tcccatgtct tccacgttaa | 900 |
| gcctccgccg cacgcctaca gcgcagcgct ggagcccttc tttgaaagcc ctctgactga | 960 |
| ttgcaccagc ccttcctttg atggacccct cagcccgccg ctcagcatca atggcaactt | 1020 |
| ctctttcaaa cacgaaccgt ccgccgagtt tgagaaaaat tatgccttta ccatgcacta | 1080 |
| tcctgcagcg acactggcag gggcccaaag ccacggatca atcttctcag gcaccgctgc | 1140 |
| ccctcgctgc gagatcccca tagacaatat tatgtccttc gatagccatt cacatcatga | 1200 |
| gcgagtcatg agtgcccagc tcaatgccat atttcatgat tagaggcacg ccagtttcac | 1260 |
| catttccggg aaacgaaccc actgtgctta cagtgactgt cgtgtttaca aaaggcagcc | 1320 |
| ctttggtact actgctgcaa agtgcaaata ctccaagctt caagtgatat atgtatttat | 1380 |
| tgtcattact gcctttggaa gaaacagggg atcaaagttc ctgttcacct tatgtattat | 1440 |
| tttctataga ctcttctatt ttaaaaaata aaaaaataca gtaaagttta aaaaatacac | 1500 |
| cacgaatttg gtgtggctgt attcagatcg tattaattat ctgatcggga taacaaaatc | 1560 |
| acaagcaata attaggatct atgcaatttt taaactagta atgggccaat taaaatatat | 1620 |
| ataaatatat atttcaacca gcattttact acttgttacc tcccatgctg aattat | 1676 |

<210> SEQ ID NO 3
<211> LENGTH: 1550
<212> TYPE: DNA
<213> ORGANISM: Human
<220> FEATURE:
<221> NAME/KEY: gene
<222> LOCATION: (0)...(0)
<223> OTHER INFORMATION: Neurogenic basic-helix-loop-helix protein (Neuro D2) gene Genbank Accession U58681
<220> FEATURE:
<221> NAME/KEY: unsure
<222> LOCATION: (1219)...(1226)
<223> OTHER INFORMATION: n at 1219 and 1226; n = A, T, G, or C

<400> SEQUENCE: 3

| | |
|---|---|
| cccctcactt tgtgctgtct gtctcccctt cccgcccgcg gggcgccctc aggcaccatg | 60 |
| ctgacccgcc tgttcagcga gcccggcctt ctctcggacg tgcccaagtt cgccagctgg | 120 |
| ggcgacggcg aagacgacga gccgaggagc gacaagggcg acgcgccgcc accgccaccg | 180 |
| cctgcgcccg ggccagggc tccggggcca gcccggggcg ccaagccagt ccctctccgt | 240 |
| ggagaagagg ggacggaggc cacgttggcc gaggtcaagg aggaaggcga gctgggggga | 300 |

```
gaggaggagg aggaagagga ggaggaagaa ggactggacg aggcggaggg cgagcggccc    360
aagaagcgcg ggcccaagaa gcgcaagatg accaaggcgc gcttggagcg ctccaagctt    420
cggcggcaga aggcgaacgc gcgggagcgc aaccgcatgc acgacctgaa cgcagccctg    480
gacaacctgc gcaaggtggt gccctgctac tccaagacgc agaagctgtc caagatcgag    540
acgctgcgcc tagccaagaa ctatatctgg gcgctctcgg agatcctgcg ctccggcaag    600
cggccagacc tagtgtccta cgtgcagact ctgtgcaagg gtctgtcgca gcccaccacc    660
aatctggtgg ccggctgtct gcagctcaac tctcgcaact tcctcacgga gcaaggcgcc    720
gacggtgccg gccgcttcca cggctcgggc ggcccgttcg ccatgcaccc ctacccgtac    780
ccgtgctcgc gcctggcggg cgcacagtgc caggcggccg gcggcctggg cggcggcgcg    840
gcgcacgccc tgcggaccca cggctactgc gccgcctacg agacgctgta tgcggcggca    900
ggcggtggcg gcgcgagccc ggactacaac agctccgagt acgagggccc gctcagcccc    960
ccgctctgtc tcaatggcaa cttctcactc aagcaggact cctcgcccga ccacgagaaa   1020
agctaccact actctatgca ctactcggcg ctgcccggtt cgcggcccac gggcacgggg   1080
ctagtcttcg gctcgtcggc tgtgcgcggg ggcgtccact cggagaatct cttgtcttac   1140
gatatgcacc ttcaccacga ccggggcccc atgtacgagg agctcaatgc gttttttcat   1200
aactgagact tcgcgccgnc tccctncttt ttcttttgcc tttgcccgcc ccctgtccc    1260 cagcccccag agcgcaggga cacccccatc ctacccggc gccgggcgcg gggagcgggc    1320
caccggtcct gccgctctcc tggggcagcg cagtcctgtt acctgtgggt ggcctgtccc   1380
aggggcctcg cttcccccag gggactcgcc ttctctcccc aagggcttcc ctcctcctct   1440
ctcccaagga gtgcttctcc agggacctct ctccggggc tccctggagg cacccctccc   1500
ccattcccaa tatcttcgct gaggtttcct cctcccccte ctccctgcag             1550

<210> SEQ ID NO 4
<211> LENGTH: 1635
<212> TYPE: DNA
<213> ORGANISM: Human
<220> FEATURE:
<221> NAME/KEY: gene
<222> LOCATION: (0)...(0)
<223> OTHER INFORMATION: Achoaete scute homologous protein (ASH1) gene;
      Genbank accession L08424

<400> SEQUENCE: 4
cccgagaccc ggcgcaagag agcgcagcct tagtaggaga ggaacgcgag acgcggcaga     60
gcgcgttcag cactgacttt tgctgctgct tctgcttttt tttttcttag aaacaagaag    120
gcgccagcgg cagcctcaca cgcgagcgcc acgcgaggct cccgaagcca acccgcgaag    180
ggaggagggg agggaggagg aggcggcgtg cagggaggag aaaaagcatt ttcaccttt     240 ttgctcccac tctaagaagt ctcccgggga ttttgtatat attttttaac ttccgtcagg    300
gctcccgctt catatttcct tttctttccc tctctgttcc tgcacccaag ttctctctgt    360 gtcccctcg cgggccccgc acctcgcgtc ccggatcgct ctgattccgc gactccttgg    420
ccgccgctgc gcatggaaag ctctgccaag atggagagcg gcggcgccgg ccagcagccc    480
cagccgcagc cccagcagcc cttcctgccg cccgcagcct gtttctttgc cacggccgca    540
gccgcggcgg ccgcagccgc cgcagcggca gcgcagagcg cgcagcagca gcagcagcag    600
cagcagcagc agcagcagca gcaggcgccg cagctgagac cggcggccga cggccagccc    660 tcaggggcg gtcacaagtc agcgcccaag caagtcaagc gacagcgctc gtcttcgccc    720
```

-continued

```
gaactgatgc gctgcaaacg ccggctcaac ttcagcggct ttggctacag cctgccgcag    780
cagcagccgg ccgccgtggc gcgccgcaac gagcgcgagc gcaaccgcgt caagttggtc    840
aacctgggct tgccaccct tcgggagcac gtccccaacg cgcggccaa caagaagatg     900 agtaaggtgg agacactgcg ctcggcggtc gagtacatcc gcgcgctgca gcagctgctg    960
gacgagcatg acgcggtgag cgccgccttc caggcaggcg tcctgtcgcc caccatctcc   1020
cccaactact ccaacgactt gaactccatg gccggctcgc cggtctcatc ctactcgtcg   1080
gacgagggct cttacgaccc gctcagcccc gaggagcagg agcttctcga cttcaccaac   1140
tggttctgag gggctcggcc tggtcaggcc ctggtgcgaa tggactttgg aagcagggtg   1200
atcgcacaac ctgcatcttt agtgctttct tgtcagtggc gttgggaggg ggagaaaagg   1260 aaagaaaaa aaagaagaa gaagaagaaa agagaagaag aaaaaaacga aaacagtcaa     1320
ccaaccccat cgccaactaa gcgaggcatg cctgagagac atggctttca gaaaacggga   1380
agcgctcaga acagtatctt tgcactccaa tcattcacgg agatatgaag agcaactggg   1440
acctgagtca atgcgcaaaa tgcagcttgt gtgcaaaagc agtgggctcc tggcagaagg   1500
gagcagcaca cgcgttatag taactcccat cacctctaac acgcacagct gaaagttctt   1560
gctcgggtcc cttcacctcc ccgccctttc ttagagtgca gttcttagcc ctctagaaac   1620
gagttggtgt ctttc                                                    1635
```

```
<210> SEQ ID NO 5
<211> LENGTH: 3138
<212> TYPE: DNA
<213> ORGANISM: Human
<220> FEATURE:
<221> NAME/KEY: gene
<222> LOCATION: (0)...(0)
<223> OTHER INFORMATION: Zic 1 Protein gene; Genbank Acession D76435

<400> SEQUENCE: 5
cgggtgccat gcagctttct ctaatttgct ctcagttcct ggctatgaat tgctaaacta     60
tcagtctcgc gctcaccgcc cggctgagga ggtgaaagtt tctccccagg aagataaacc    120
gcaaaagaca tatattgtgc atgatttgcg cctttcttt ggcttttct ttctttcttc      180 accccccac ccacttttttt tttttttttt ttcaaaaagc agagagggaa aaacggagag    240
tgaaggagcg aggaggcgag cgtgagagaa aggagagaga gagaaaagaa agggcgaggg    300
gctagtggag gaaggaagga ggggcggctg cgcgaggcgg agagagggcg aagcagtcgc    360
ggcactggcg ctcacattcc tctatgctac aaatccagga ggaagttttt ttttaggggg    420
ctgagatgct ccatgccttt aaaagggcag ccttgacgcg cggccctctc ggcagagact    480
gagcggcgag aaagtgcgag ccgggccggc agaatctgcc tggcgggcgc tggagcctgc    540
gttactcgcg gcccgcagcc gtccggctac tttgcgtttg gccggccag cgccgcgcgg     600 cgcgcgcgcg ccattgcctg caggctagga cttcgcgagg tgggtcgact cacctccct    660 cctcctcttc ttcctcctct tcctcctcct cttgttcctc ctcctcctcc cgattttccc    720
tcctcggctg gcgagggtgg gggggcggg ggaggccggg gctcgccccg agcagccacg     780
atgctcctgg acgccggccc ccagtacccA gcgatcggcg tgaccaccct tggcgcgtcc    840
cgccaccact ccgcgggcga cgtggccgaa cgagacgtgg gcctgggcat caacccgttc    900
gccgacggca tggcgccctt caagctcaac cccagttcgc acgagctggc ttcgccggc    960 cagacagcct tcacgtcgca ggcgccaggc tacgcggctg ctgcgccct gggccatcac   1020 catcacccgg gccacgtcgg ctcctattcc agcgcagcct tcaactccac gcgggacttt   1080
```

-continued

```
ctgttccgca accggggttt tggcgacgcg gcggcggcag ccagcgcaca gcacagcctc    1140
tttgctgcat cggccggggg cttcgggggc ccacacggcc acacggacgc cgcgggccac    1200
ctcctcttcc ccgggcttca cgagcaggct gccggccacg cgtcgcctaa cgtggtcaac    1260
gggcagatga ggctcggctt ctcggggac atgtacccgc gaccggagca gtacggccag    1320
gtgaccagcc cgcgttcgga gcactatgct gcgccgcagc tgcacggcta cgggcccatg    1380
aacgtgaaca tggccgcgca tcacggcgcc ggcgccttct ccgctacat gcgccaaccc    1440 atcaagcaag agctcatctg caagtggatc gagcccgagc agctggccaa ccccaaaaag    1500
tcgtgcaaca aaactttcag caccatgcac gagctagtta cgcacgtcac cgtggagcac    1560
gtaggtggcc cggagcagag taatcacatc tgcttctggg aggagtgtcc gcgcgagggc    1620
aagcccttca agccaaata caaactggtt aaccacatcc gcgtgcacac gggcgagaag    1680
ccctttccct gccccttccc tggctgtggc aaggtcttcg cgcgctccga gaatttaaag    1740
atccacaaaa ggacgcacac aggggagaag cccttcaagt gcgagtttga gggctgtgac    1800
cggcgcttcg ctaacagcag cgaccgcaag aagcacatgc acgtgcacac gagcgacaag    1860
ccctatcttt gcaagatgtg cgacaagtcc tacacgcatc ccagttccgt gcgcaaacac    1920
atgaaggtcc acgaatcctc ctcgcagggc tcgcagcctt cgccggccgc cagctctggc    1980
tacgaatcct ccacgcctcc caccatcgtg tctccctcca cagacaaccc gaccacaagc    2040
tccttatcgc cctcctcctc cgcagtccac cacacagccg ccacagtgc gctctcttcc    2100 aattttaacg aatggtacgt ttaaaatcag aaacaaaaca tcgaacaaaa ccctatttaa    2160
gagacttgat cacacacgta tacacaacat tactgaaaga accctgcgaa tcaaaacaac    2220
ccccacacag accccgcaat cctctttttaa aaaatctgcc aatagaccca ggacgagtaa    2280
gagaggaagc atcaaccttt taaaaatttc ctttcgcttt cattattttt cttttttttgg    2340 caaaggcttg gtacccaagg tgcggtaggg ggtcgagggg gaggaggcca cctgaccaaa    2400
tgccgccaac cccgagggcc agtttcttgt cgaattggta cgggctctct ggggcttcgg    2460 cttcttttttt tctttgtttt cttgtaaata cagaattatt agcttaaaac tgtactgttg    2520
aattctgtaa atagttatat ctcgttggga gcggtgggt gggattgtgg cgttgtggtc    2580
tttgcattgg gggaggggggg agggaccgga tgggcggggg gaggggagg gggaggggtg    2640 ggcggccgaa agccaactgt ttgtactgaa tggcaagaat gttctagtaa atgtgtacca    2700
aaatgtgaat tactttgtac gattacagtc tccacgtcga cctaacccaa tattattggt    2760
attaatgtgc ttttttttgta taaagtgcaa acatttcgtc ccaaagtcta agtactttag    2820
tgcagtaaaa tgttgtttca tgtcctgtca agaattcgta tagtacgagc ctggatctgc    2880
gtgtcaaact gttccatttg tttatgtaaa gtgatattaa aaaagatata aactataact    2940
gtccgttact tttggcaaaa gatacaacca cataatgtat ataattccta gtttccatat    3000
ttatccgcat gtaaagggcc ggtttatcca tgttacagct cttcaatatt tatggctaga    3060
agaactcgta tgtacacttt agtttccaga actgtttggt aacctttcgt accttattaa    3120
agattcttaa atctcaaa                                                  3138
```

```
<210> SEQ ID NO 6
<211> LENGTH: 2623
<212> TYPE: DNA
<213> ORGANISM: Human
<220> FEATURE:
<221> NAME/KEY: gene
<222> LOCATION: (0)...(0)
```

<223> OTHER INFORMATION: Myelin transcription factor 1 (MyT1) gene Genbank
      Accession M96980

<400> SEQUENCE: 6

```
cggaagagtt actacagtaa agatccttca agagctgaga agcgtgagat caagtgtcca      60
acaccaggct gtgatggcac tggccacgtt accgggttgt accctcacca ccgcagcctt     120
tctggctgtc cccacaagga taggatcccc ccagagatct tagccatgca tgagaacgtg     180
ctgaagtgcc ccactcctgg ctgcacaggc cagggtcacg tgaacagcaa ccgcaacacg     240
cacagaagtt tgtctgggtg tcccattgct gccgccgaaa aattagccaa atcccatgag     300
aagcagcagc cgcagacagg agatccttcc aagagtagct ccaattccga tcggatcctc     360
aggcccatgt gcttcgtgaa gcagctcgag gtccctccat atgggagcta ccggcccaac     420
gtggccccc gccacaccca gggccaactt ggcaaggagc tggagaagtt ctccaaggtc     480
acctttgact acgcaagttt cgatgctcag gttttggca aacgcatgct tgccccaaag     540
attcagacca gcgaaacctc acctaaagcc tttcaatcca aacctttccc aaaggcctct     600
tccccaggc acagccctc cagtagttat gtgaggagca cttcatcctc ttctgcaggc     660
tttgactact cgcaggacgc cgaggctgca cacatggctg ccactgccat cctgaacctc     720
tccacgcgct gctgggagat gcctgagaac ctcagcacga agccacagga cctccccagc     780
aagtctgtgg atatcgaggt agacgaaaat ggaaccctgg acttgagcat gcacaaacac     840
cgcaaacgag aaaatgcttt ccccagcagc agcagctgca gcagcagccc cggtgtgaag     900
tctcccgacg cctcccagcg ccacagcagc accagcgccc cagcagctc catgacctct     960
ccccagtcca gccaggcctc ccgccaggac gagtgggacc ggcccctgga ctacaccaag    1020
cctagccgcc tgagagagga ggaacctgag gagtcagagc cagcagccca ttcttttgct    1080
tcttctgaag cagatgacca ggaagtgtcg gaagagaatt ttgaggagcg gaagtatccg    1140
ggggaagtca ccctgaccaa ctttaagctg aagtttctct ccaaggacat aaagaaggag    1200
ctgctcacct gtcccacccc tggctgtgac ggcagcggcc acatcaccgg gaactacgcc    1260
tcccaccgca gcctctctgg ttgccctctt gctgacaaga gcctcagaaa cctcatggct    1320
acccactctg ctgacctgaa gtgccccacg cccggctgtg acggctctgg ccacatcaca    1380
gggaactacg cttcacaccg gagcttgtcc ggctgccctc gtgcaaagaa aagtggagtc    1440
aaggtggcac ccaccaagga cgacaaggag accccgagc tgatgaagtg cccagttcca    1500
ggctgtgtgg ggctcggtca catcagcggg aaatacgcct ctcacaggag cgcatccggc    1560
tgccccactgg ccgcccgcag gcagaaggaa gggtccctca atggctcgtc attctcctgg    1620
aagtccctga agaatgaaga cccgacctgc cccaccccgg gctgtgacgg ctctggccac    1680
accattggga gtttcctcac ccaccggagt ttgtcaggct gtcccagagc aacctttgct    1740
ggaaagaagg gaaaactgtc aggggatgag gtcctcagtc caaagttcaa gactagcgac    1800
gtgttggaga tgatgaggaa gatcaagcag ctgaaccagg agatccgaga cctgaacgag    1860
tccaactcga gatgaggc tgccatggtg cagctgcagt cccagatctc ctccatggag    1920
aagaacctga gaacatcga ggaggagaac aagctcattg aggagcagaa tgaagccctg    1980
tttctggagc tgtccggcct gagccaggcc ctcatccaaa gtctcgccaa tatccacctt    2040
ccacacatgg agccaatatg cgaacagaat ttcgttccct atgtgagcac cctcaccgac    2100
atgtactcca accaggcccc ggagaacaag gacctcctgg agagcatcaa gcaggctgtg    2160
agggggcatcc aggtctaggc cgtgtggtac ccagaagtgt cccagcccac cacaccgttt    2220
```

```
acctccctcg ccctgccccg caccgtgggg atgcccaact cacagtgact tcccgtttgg    2280
ggcccggtgt ggcgcgggcg ggtttatcca aagggatggc tggaaattgg ccgctcccac    2340
gaggctccct ccaggcttgg ccgtggtggc cctatctgtg tgcataggggg cactgaagaa    2400 ttacaaagtg atttattttt gttttctgaa agaaatctga agagcagctc aaagtctcca    2460
gtggaagctc atggacaagg ttctcaggga agttttggag tttgcaacca cagtattcct    2520
ttgtctgtcg aggctgggag ggtagccgtg agcgtggtgg gtgggtggtg tgagtggcat    2580
cttggcctgg agtacacgcc tggggcagcg tgtctgtgct cag                      2623
```

<210> SEQ ID NO 7
<211> LENGTH: 356
<212> TYPE: PRT
<213> ORGANISM: Human
<220> FEATURE:
<221> NAME/KEY: PEPTIDE
<222> LOCATION: (0)...(0)
<223> OTHER INFORMATION: Neuro D1 protein; Genbank Accession D82347

<400> SEQUENCE: 7

```
Met Thr Lys Ser Tyr Ser Glu Ser Gly Leu Met Gly Glu Pro Gln Pro
  1               5                  10                  15

Gln Gly Pro Pro Ser Trp Thr Asp Glu Cys Leu Ser Ser Gln Asp Glu
                 20                  25                  30

Glu His Glu Ala Asp Lys Lys Glu Asp Asp Leu Glu Ala Met Asn Ala
             35                  40                  45

Glu Glu Asp Ser Leu Arg Asn Gly Gly Glu Glu Asp Glu Asp Glu
         50                  55                  60

Asp Leu Glu Glu Glu Glu Glu Glu Glu Glu Asp Asp Asp Gln Lys
 65                  70                  75                  80

Pro Lys Arg Arg Gly Pro Lys Lys Lys Met Thr Lys Ala Arg Leu
                 85                  90                  95

Glu Arg Phe Lys Leu Arg Arg Met Lys Ala Asn Ala Arg Glu Arg Asn
                100                 105                 110

Arg Met His Gly Leu Asn Ala Ala Leu Asp Asn Leu Arg Lys Val Val
            115                 120                 125

Pro Cys Tyr Ser Lys Thr Gln Lys Leu Ser Lys Ile Glu Thr Leu Arg
130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Gly Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285
```

```
Pro Ser Ala Glu Phe Glu Lys Asn Tyr Ala Phe Thr Met His Tyr Pro
    290                 295                 300
Ala Ala Thr Leu Ala Gly Ala Gln Ser His Gly Ser Ile Phe Ser Gly
305                 310                 315                 320
Thr Ala Ala Pro Arg Cys Glu Ile Pro Ile Asp Asn Ile Met Ser Phe
                325                 330                 335
Asp Ser His Ser His His Glu Arg Val Met Ser Ala Gln Leu Asn Ala
                340                 345                 350
Ile Phe His Asp
        355

<210> SEQ ID NO 8
<211> LENGTH: 356
<212> TYPE: PRT
<213> ORGANISM: Human
<220> FEATURE:
<221> NAME/KEY: PEPTIDE
<222> LOCATION: (0)...(0)
<223> OTHER INFORMATION: Neurogenic basic helix-loop-helix protein (Neurod
      1); Genbank Accession U50822.

<400> SEQUENCE: 8

Met Thr Lys Ser Tyr Ser Glu Ser Gly Leu Met Gly Glu Pro Gln Pro
1               5                   10                  15
Gln Gly Pro Pro Ser Trp Thr Asp Glu Cys Leu Ser Ser Gln Asp Glu
                20                  25                  30
Glu His Glu Ala Asp Lys Lys Glu Asp Asp Leu Glu Ala Met Asn Ala
            35                  40                  45
Glu Glu Asp Ser Leu Arg Asn Gly Gly Glu Glu Asp Glu Asp
50                  55                  60
Asp Leu Glu Glu Glu Glu Glu Glu Glu Glu Asp Asp Gln Lys
65                  70                  75                  80
Pro Lys Arg Arg Gly Pro Lys Lys Lys Met Thr Lys Ala Arg Leu
                85                  90                  95
Glu Arg Phe Lys Leu Arg Arg Met Lys Ala Asn Ala Arg Glu Arg Asn
            100                 105                 110
Arg Met His Gly Leu Asn Ala Ala Leu Asp Asn Leu Arg Lys Val Val
            115                 120                 125
Pro Cys Tyr Ser Lys Thr Gln Lys Leu Ser Lys Ile Glu Thr Leu Arg
130                 135                 140
Leu Ala Lys Asn Tyr Ile Trp Ala Leu Ser Glu Ile Ser Arg Ser Gly
145                 150                 155                 160
Lys Ser Pro Asp Leu Val Ser Phe Val Gln Thr Leu Cys Lys Gly Leu
                165                 170                 175
Ser Gln Pro Thr Thr Asn Leu Val Ala Gly Cys Leu Gln Leu Asn Pro
            180                 185                 190
Arg Thr Phe Leu Pro Glu Gln Asn Gln Asp Met Pro Pro His Leu Pro
            195                 200                 205
Thr Ala Ser Ala Ser Phe Pro Val His Pro Tyr Ser Tyr Gln Ser Pro
210                 215                 220
Gly Leu Pro Ser Pro Pro Tyr Gly Thr Met Asp Ser Ser His Val Phe
225                 230                 235                 240
His Val Lys Pro Pro Pro His Ala Tyr Ser Ala Ala Leu Glu Pro Phe
                245                 250                 255
Phe Glu Ser Pro Leu Thr Asp Cys Thr Ser Pro Ser Phe Asp Gly Pro
            260                 265                 270
```

-continued

```
Leu Ser Pro Pro Leu Ser Ile Asn Gly Asn Phe Ser Phe Lys His Glu
            275                 280                 285

Pro Ser Ala Glu Phe Glu Lys Asn Tyr Ala Phe Thr Met His Tyr Pro
        290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 9
<211> LENGTH: 382
<212> TYPE: PRT
<213> ORGANISM: Human
<220> FEATURE:
<221> NAME/KEY: PEPTIDE
<222> LOCATION: (0)...(0)
<223> OTHER INFORMATION: Neurogenic basic helix-loop-helix protein (neuro
      D2); Genbank Accession U58681.

<400> SEQUENCE: 9

Met Leu Thr Arg Leu Phe Ser Glu Pro Gly Leu Leu Ser Asp Val Pro
1               5                   10                  15

Lys Phe Ala Ser Trp Gly Asp Gly Glu Asp Asp Glu Pro Arg Ser Asp
            20                  25                  30

Lys Gly Asp Ala Pro Pro Pro Pro Ala Pro Gly Pro Gly Ala
        35                  40                  45

Pro Gly Pro Ala Arg Ala Ala Lys Pro Val Pro Leu Arg Gly Glu Glu
    50                  55                  60

Gly Thr Glu Ala Thr Leu Ala Glu Val Lys Glu Gly Glu Leu Gly
65                  70                  75                  80

Gly Glu Glu Glu Glu Glu Glu Glu Glu Gly Leu Asp Glu Ala
            85                  90                  95

Glu Gly Glu Arg Pro Lys Lys Arg Gly Pro Lys Lys Arg Lys Met Thr
            100                 105                 110

Lys Ala Arg Leu Glu Arg Ser Lys Leu Arg Arg Gln Lys Ala Asn Ala
        115                 120                 125

Arg Glu Arg Asn Arg Met His Asp Leu Asn Ala Ala Leu Asp Asn Leu
130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
            180                 185                 190

Cys Lys Gly Leu Ser Gln Pro Thr Thr Asn Leu Val Ala Gly Cys Leu
        195                 200                 205

Gln Leu Asn Ser Arg Asn Phe Leu Thr Glu Gln Gly Ala Asp Gly Ala
    210                 215                 220

Gly Arg Phe His Gly Ser Gly Gly Pro Phe Ala Met His Pro Tyr Pro
225                 230                 235                 240

Tyr Pro Cys Ser Arg Leu Ala Gly Ala Gln Cys Gln Ala Ala Gly Gly
                245                 250                 255
```

```
Leu Gly Gly Gly Ala Ala His Ala Leu Arg Thr His Gly Tyr Cys Ala
            260                 265                 270

Ala Tyr Glu Thr Leu Tyr Ala Ala Gly Gly Gly Ala Ser Pro
        275                 280                 285

Asp Tyr Asn Ser Ser Glu Tyr Glu Gly Pro Leu Ser Pro Leu Cys
        290                 295                 300

Leu Asn Gly Asn Phe Ser Leu Lys Gln Asp Ser Ser Pro Asp His Glu
305                 310                 315                 320

Lys Ser Tyr His Tyr Ser Met His Tyr Ser Ala Leu Pro Gly Ser Arg
                325                 330                 335

Pro Thr Gly His Gly Leu Val Phe Gly Ser Ser Ala Val Arg Gly Gly
                340                 345                 350

Val His Ser Glu Asn Leu Leu Ser Tyr Asp Met His Leu His His Asp
        355                 360                 365

Arg Gly Pro Met Tyr Glu Glu Leu Asn Ala Phe Phe His Asn
        370                 375                 380

<210> SEQ ID NO 10
<211> LENGTH: 238
<212> TYPE: PRT
<213> ORGANISM: Human
<220> FEATURE:
<221> NAME/KEY: PEPTIDE
<222> LOCATION: (0)...(0)
<223> OTHER INFORMATION: Achaete scute homologous protein (ASH1); Genbank
      Accession L08424.

<400> SEQUENCE: 10

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Gln Gln
    50                  55                  60

Ala Pro Gln Leu Arg Pro Ala Ala Asp Gly Gln Pro Ser Gly Gly Gly
65                  70                  75                  80

His Lys Ser Ala Pro Lys Gln Val Lys Arg Gln Arg Ser Ser Ser Pro
                85                  90                  95

Glu Leu Met Arg Cys Lys Arg Arg Leu Asn Phe Ser Gly Phe Gly Tyr
            100                 105                 110

Ser Leu Pro Gln Gln Gln Pro Ala Ala Val Ala Arg Arg Asn Glu Arg
        115                 120                 125

Glu Arg Asn Arg Val Lys Leu Val Asn Leu Gly Phe Ala Thr Leu Arg
130                 135                 140

Glu His Val Pro Asn Gly Ala Ala Asn Lys Lys Met Ser Lys Val Glu
145                 150                 155                 160

Thr Leu Arg Ser Ala Val Glu Tyr Ile Arg Ala Leu Gln Gln Leu Leu
                165                 170                 175

Asp Glu His Asp Ala Val Ser Ala Ala Phe Gln Ala Gly Val Leu Ser
            180                 185                 190

Pro Thr Ile Ser Pro Asn Tyr Ser Asn Asp Leu Asn Ser Met Ala Gly
        195                 200                 205

Ser Pro Val Ser Ser Tyr Ser Ser Asp Glu Gly Ser Tyr Asp Pro Leu
    210                 215                 220
```

```
Ser Pro Glu Glu Gln Glu Leu Leu Asp Phe Thr Asn Trp Phe
225                 230                 235
```

<210> SEQ ID NO 11
<211> LENGTH: 447
<212> TYPE: PRT
<213> ORGANISM: Human
<220> FEATURE:
<221> NAME/KEY: PEPTIDE
<222> LOCATION: (0)...(0)
<223> OTHER INFORMATION: Zic 1 protein; Genbank Accession D76435.

<400> SEQUENCE: 11

```
Met Leu Leu Asp Ala Gly Pro Gln Tyr Pro Ala Ile Gly Val Thr Thr
1               5                   10                  15

Phe Gly Ala Ser Arg His His Ser Ala Gly Asp Val Ala Glu Arg Asp
                20                  25                  30

Val Gly Leu Gly Ile Asn Pro Phe Ala Asp Gly Met Gly Ala Phe Lys
            35                  40                  45

Leu Asn Pro Ser Ser His Glu Leu Ala Ser Ala Gly Gln Thr Ala Phe
        50                  55                  60

Thr Ser Gln Ala Pro Gly Tyr Ala Ala Ala Ala Leu Gly His His
65                  70                  75                  80

His His Pro Gly His Val Gly Ser Tyr Ser Ala Ala Phe Asn Ser
                85                  90                  95

Thr Arg Asp Phe Leu Phe Arg Asn Arg Gly Phe Gly Asp Ala Ala Ala
                100                 105                 110

Ala Ala Ser Ala Gln His Ser Leu Phe Ala Ala Ser Ala Gly Gly Phe
            115                 120                 125

Gly Gly Pro His Gly His Thr Asp Ala Ala Gly His Leu Leu Phe Pro
130                 135                 140

Gly Leu His Glu Gln Ala Ala Gly His Ala Ser Pro Asn Val Val Asn
145                 150                 155                 160

Gly Gln Met Arg Leu Gly Phe Ser Gly Asp Met Tyr Pro Arg Pro Glu
                165                 170                 175

Gln Tyr Gly Gln Val Thr Ser Pro Arg Ser Glu His Tyr Ala Ala Pro
            180                 185                 190

Gln Leu His Gly Tyr Gly Pro Met Asn Val Asn Met Ala Ala His His
        195                 200                 205

Gly Ala Gly Ala Phe Phe Arg Tyr Met Arg Gln Pro Ile Lys Gln Glu
210                 215                 220

Leu Ile Cys Lys Trp Ile Glu Pro Glu Gln Leu Ala Asn Pro Lys Lys
225                 230                 235                 240

Ser Cys Asn Lys Thr Phe Ser Thr Met His Glu Leu Val Thr His Val
                245                 250                 255

Thr Val Glu His Val Gly Gly Pro Glu Gln Ser Asn His Ile Cys Phe
            260                 265                 270

Trp Glu Glu Cys Pro Arg Glu Gly Lys Pro Phe Lys Ala Lys Tyr Lys
        275                 280                 285

Leu Val Asn His Ile Arg Val His Thr Gly Glu Lys Pro Phe Pro Cys
    290                 295                 300

Pro Phe Pro Gly Cys Gly Lys Val Phe Ala Arg Ser Glu Asn Leu Lys
305                 310                 315                 320

Ile His Lys Arg Thr His Thr Gly Glu Lys Pro Phe Lys Cys Glu Phe
                325                 330                 335
```

-continued

```
Glu Gly Cys Asp Arg Arg Phe Ala Asn Ser Ser Asp Arg Lys Lys His
            340                 345                 350

Met His Val His Thr Ser Asp Lys Pro Tyr Leu Cys Lys Met Cys Asp
        355                 360                 365

Lys Ser Tyr Thr His Pro Ser Ser Val Arg Lys His Met Lys Val His
    370                 375                 380

Glu Ser Ser Ser Gln Gly Ser Gln Pro Ser Pro Ala Ala Ser Ser Gly
385                 390                 395                 400

Tyr Glu Ser Ser Thr Pro Pro Thr Ile Val Ser Pro Ser Thr Asp Asn
                405                 410                 415

Pro Thr Thr Ser Ser Leu Ser Pro Ser Ser Ser Ala Val His His Thr
                420                 425                 430

Ala Gly His Ser Ala Leu Ser Ser Asn Phe Asn Glu Trp Tyr Val
            435                 440                 445

<210> SEQ ID NO 12
<211> LENGTH: 725
<212> TYPE: PRT
<213> ORGANISM: Human
<220> FEATURE:
<221> NAME/KEY: PEPTIDE
<222> LOCATION: (0)...(0)
<223> OTHER INFORMATION: Myelin transcription factor 1 (My T1); Genbank
      Accession M96980.

<400> SEQUENCE: 12

Arg Lys Ser Tyr Tyr Ser Lys Asp Pro Ser Arg Ala Glu Lys Arg Glu
1               5                   10                  15

Ile Lys Cys Pro Thr Pro Gly Cys Asp Gly Thr Gly His Val Thr Gly
            20                  25                  30

Leu Tyr Pro His His Arg Ser Leu Ser Gly Cys Pro His Lys Asp Arg
        35                  40                  45

Ile Pro Pro Glu Ile Leu Ala Met His Glu Asn Val Leu Lys Cys Pro
    50                  55                  60

Thr Pro Gly Cys Thr Gly Gln Gly His Val Asn Ser Asn Arg Asn Thr
65                  70                  75                  80

His Arg Ser Leu Ser Gly Cys Pro Ile Ala Ala Ala Glu Lys Leu Ala
                85                  90                  95

Lys Ser His Glu Lys Gln Gln Pro Gln Thr Gly Asp Pro Ser Lys Ser
            100                 105                 110

Ser Ser Asn Ser Asp Arg Ile Leu Arg Pro Met Cys Phe Val Lys Gln
        115                 120                 125

Leu Glu Val Pro Pro Tyr Gly Ser Tyr Arg Pro Asn Val Ala Pro Arg
130                 135                 140

His Thr Gln Gly Gln Leu Gly Lys Glu Leu Glu Lys Phe Ser Lys Val
145                 150                 155                 160

Thr Phe Asp Tyr Ala Ser Phe Asp Ala Gln Val Phe Gly Lys Arg Met
                165                 170                 175

Leu Ala Pro Lys Ile Gln Thr Ser Glu Thr Ser Pro Lys Ala Phe Gln
            180                 185                 190

Ser Lys Pro Phe Pro Lys Ala Ser Ser Pro Arg His Ser Pro Ser Ser
        195                 200                 205

Ser Tyr Val Arg Ser Thr Ser Ser Ser Ala Gly Phe Asp Tyr Ser
    210                 215                 220

Gln Asp Ala Glu Ala Ala His Met Ala Ala Thr Ala Ile Leu Asn Leu
225                 230                 235                 240
```

-continued

```
Ser Thr Arg Cys Trp Glu Met Pro Glu Asn Leu Ser Thr Lys Pro Gln
                245                 250                 255

Asp Leu Pro Ser Lys Ser Val Asp Ile Glu Val Asp Glu Asn Gly Thr
            260                 265                 270

Leu Asp Leu Ser Met His Lys His Arg Lys Arg Glu Asn Ala Phe Pro
        275                 280                 285

Ser Ser Ser Ser Cys Ser Ser Pro Gly Val Lys Ser Pro Asp Ala
    290                 295                 300

Ser Gln Arg His Ser Ser Thr Ser Ala Pro Ser Ser Met Thr Ser
305                 310                 315                 320

Pro Gln Ser Ser Gln Ala Ser Arg Gln Asp Glu Trp Asp Arg Pro Leu
                325                 330                 335

Asp Tyr Thr Lys Pro Ser Arg Leu Arg Glu Glu Pro Glu Glu Ser
            340                 345                 350

Glu Pro Ala Ala His Ser Phe Ala Ser Ser Glu Ala Asp Asp Gln Glu
        355                 360                 365

Val Ser Glu Glu Asn Phe Glu Glu Arg Lys Tyr Pro Gly Glu Val Thr
    370                 375                 380

Leu Thr Asn Phe Lys Leu Lys Phe Leu Ser Lys Asp Ile Lys Lys Glu
385                 390                 395                 400

Leu Leu Thr Cys Pro Thr Pro Gly Cys Asp Gly Ser Gly His Ile Thr
                405                 410                 415

Gly Asn Tyr Ala Ser His Arg Ser Leu Ser Gly Cys Pro Leu Ala Asp
            420                 425                 430

Lys Ser Leu Arg Asn Leu Met Ala Thr His Ser Ala Asp Leu Lys Cys
        435                 440                 445

Pro Thr Pro Gly Cys Asp Gly Ser Gly His Ile Thr Gly Asn Tyr Ala
    450                 455                 460

Ser His Arg Ser Leu Ser Gly Cys Pro Arg Ala Lys Lys Ser Gly Val
465                 470                 475                 480

Lys Val Ala Pro Thr Lys Asp Asp Lys Glu Asp Pro Glu Leu Met Lys
                485                 490                 495

Cys Pro Val Pro Gly Cys Val Gly Leu Gly His Ile Ser Gly Lys Tyr
            500                 505                 510

Ala Ser His Arg Ser Ala Ser Gly Cys Pro Leu Ala Ala Arg Arg Gln
        515                 520                 525

Lys Glu Gly Ser Leu Asn Gly Ser Ser Phe Ser Trp Lys Ser Leu Lys
    530                 535                 540

Asn Glu Asp Pro Thr Cys Pro Thr Pro Gly Cys Asp Gly Ser Gly His
545                 550                 555                 560

Thr Ile Gly Ser Phe Leu Thr His Arg Ser Leu Ser Gly Cys Pro Arg
                565                 570                 575

Ala Thr Phe Ala Gly Lys Lys Gly Lys Leu Ser Gly Asp Glu Val Leu
            580                 585                 590

Ser Pro Lys Phe Lys Thr Ser Asp Val Leu Glu Asn Asp Glu Glu Ile
        595                 600                 605

Lys Gln Leu Asn Gln Glu Ile Arg Asp Leu Asn Glu Ser Asn Ser Glu
    610                 615                 620

Met Glu Ala Ala Met Val Gln Leu Gln Ser Gln Ile Ser Ser Met Glu
625                 630                 635                 640

Lys Asn Leu Lys Asn Ile Glu Glu Asn Lys Leu Ile Glu Glu Gln
                645                 650                 655

Asn Glu Ala Leu Phe Leu Glu Leu Ser Gly Leu Ser Gln Ala Leu Ile
```

-continued

```
            660                665                670
Gln Ser Leu Ala Asn Ile His Leu Pro His Met Glu Pro Ile Cys Glu
            675                680                685

Gln Asn Phe Val Pro Tyr Val Ser Thr Leu Thr Asp Met Tyr Ser Asn
        690                695                700

Gln Ala Pro Glu Asn Lys Asp Leu Leu Glu Ser Ile Lys Gln Ala Val
705                710                715                720

Arg Gly Ile Gln Val
                725

<210> SEQ ID NO 13
<211> LENGTH: 27
<212> TYPE: DNA
<213> ORGANISM: human
<220> FEATURE:
<221> NAME/KEY: gene
<222> LOCATION: (0)...(0)
<223> OTHER INFORMATION: MSX1 antisense oligonucleotide sequence MSX1-1

<400> SEQUENCE: 13
gacaccgagt ggcaaagaag tcatgtc                                    27

<210> SEQ ID NO 14
<211> LENGTH: 24
<212> TYPE: DNA
<213> ORGANISM: human
<220> FEATURE:
<221> NAME/KEY: gene
<222> LOCATION: (0)...(0)
<223> OTHER INFORMATION: MSX1 antisense oligonucleotide sequence MSX1-2

<400> SEQUENCE: 14
cggcttcctg tggtcggcca tgag                                       24

<210> SEQ ID NO 15
<211> LENGTH: 35
<212> TYPE: DNA
<213> ORGANISM: human
<220> FEATURE:
<221> NAME/KEY: gene
<222> LOCATION: (0)...(0)
<223> OTHER INFORMATION: HES1 open reading frame 5' sequence (HES1-1)

<400> SEQUENCE: 15
accggggacg aggaattttt ctccattata tcagc                           35

<210> SEQ ID NO 16
<211> LENGTH: 40
<212> TYPE: DNA
<213> ORGANISM: human
<220> FEATURE:
<221> NAME/KEY: gene
<222> LOCATION: (0)...(0)
<223> OTHER INFORMATION: HES1 open reading frame middle sequence (HES1-2)

<400> SEQUENCE: 16
cacggaggtg ccgctgttgc tgggctggtg tggtgtagac                      40
```